US009539116B2

(12) United States Patent
Claypool et al.

(10) Patent No.: US 9,539,116 B2
(45) Date of Patent: Jan. 10, 2017

(54) USER INTERFACE RELATED TO A SURGICAL PROVISIONAL

(75) Inventors: Jody Claypool, Columbia City, IN (US); Joel Zuhars, Warsaw, IN (US); Stuart Sullivan, Peru, IN (US); David B. Rich, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 179 days.

(21) Appl. No.: 13/819,116

(22) PCT Filed: Dec. 12, 2011

(86) PCT No.: PCT/US2011/064435
§ 371 (c)(1),
(2), (4) Date: May 9, 2013

(87) PCT Pub. No.: WO2012/082628
PCT Pub. Date: Jun. 21, 2012

(65) Prior Publication Data
US 2013/0253378 A1    Sep. 26, 2013

Related U.S. Application Data

(60) Provisional application No. 61/424,222, filed on Dec. 17, 2010.

(51) Int. Cl.
*A61F 2/46* (2006.01)
*A61F 2/38* (2006.01)
(Continued)

(52) U.S. Cl.
CPC ........... *A61F 2/4684* (2013.01); *A61B 5/1036* (2013.01); *A61F 2/30734* (2013.01); *A61F 2/389* (2013.01);
(Continued)

(58) Field of Classification Search
CPC .............................. A61B 5/1036; A61B 5/103
See application file for complete search history.

(56) References Cited

U.S. PATENT DOCUMENTS

| 4,501,266 A | 2/1985 | McDaniel |
| 4,944,757 A | 7/1990 | Martinez et al. |

(Continued)

FOREIGN PATENT DOCUMENTS

| AU | 2011343440 B2 | 4/2014 |
| CN | 1174498 A | 2/1998 |

(Continued)

OTHER PUBLICATIONS

"U.S. Appl. No. 13/836,586, Express Abandonment filed May 30, 2014", 1 pg.

(Continued)

*Primary Examiner* — Adam J Eiseman
*Assistant Examiner* — Yasmeen S Warsi
(74) *Attorney, Agent, or Firm* — Schwegman Lundberg & Woessner, P.A.

(57) ABSTRACT

Systems and methods for presenting force information related to a provisional is disclosed. A user interface may be provided for presenting objects on a display related to a knee joint, the user interface including a representation of an area of the knee joint for presentment on the display and a force center indicator for presentment on the display. The user interface providing an indication of when a position of the force center indicator corresponds to a desired position of the force center indicator.

16 Claims, 25 Drawing Sheets

(51) Int. Cl.
*A61B 5/103* (2006.01)
*A61F 2/30* (2006.01)
(52) U.S. Cl.
CPC .... *A61F 2/3868* (2013.01); *A61F 2002/30556* (2013.01)

(56) References Cited

U.S. PATENT DOCUMENTS

| | | | |
|---|---|---|---|
| 5,197,488 A | 3/1993 | Kovacevic | |
| 5,344,461 A | 9/1994 | Phlipot | |
| 5,360,016 A | 11/1994 | Kovacevic | |
| 5,364,402 A | 11/1994 | Mumme et al. | |
| 5,387,239 A | 2/1995 | Bianco et al. | |
| 5,395,401 A | 3/1995 | Bahler | |
| 5,425,775 A | 6/1995 | Kovacevic et al. | |
| 5,458,637 A | 10/1995 | Hayes | |
| 5,470,354 A | 11/1995 | Hershberger et al. | |
| 5,489,311 A | 2/1996 | Cipolletti | |
| 5,571,194 A | 11/1996 | Gabriel | |
| 5,609,645 A | 3/1997 | Vinciguerra | |
| 5,656,785 A | 8/1997 | Trainor et al. | |
| 5,658,341 A | 8/1997 | Delfosse | |
| 5,702,464 A | 12/1997 | Lackey et al. | |
| 5,733,292 A | 3/1998 | Gustilo et al. | |
| 5,776,200 A | 7/1998 | Johnson et al. | |
| 5,782,925 A | 7/1998 | Collazo et al. | |
| 5,824,103 A | 10/1998 | Williams et al. | |
| 5,871,541 A | 2/1999 | Gerber | |
| 5,976,147 A | 11/1999 | LaSalle et al. | |
| 6,126,692 A | 10/2000 | Robie et al. | |
| 6,607,559 B2 | 8/2003 | Ralph et al. | |
| 6,632,225 B2 | 10/2003 | Sanford et al. | |
| 6,702,821 B2 | 3/2004 | Bonutti | |
| 6,743,258 B1 | 6/2004 | Keller | |
| 6,770,078 B2 | 8/2004 | Bonutti | |
| 6,942,670 B2 | 9/2005 | Heldreth et al. | |
| 6,974,481 B1 | 12/2005 | Carson | |
| 7,309,363 B2 | 12/2007 | Dietz | |
| 7,412,897 B2 | 8/2008 | Crottet et al. | |
| 7,442,196 B2 | 10/2008 | Fisher et al. | |
| 7,488,330 B2 | 2/2009 | Stad | |
| 7,547,327 B2 | 6/2009 | Collazo | |
| 7,575,602 B2 | 8/2009 | Amirouche et al. | |
| 7,578,821 B2 | 8/2009 | Fisher et al. | |
| 7,587,945 B2 | 9/2009 | Crottet et al. | |
| 7,591,854 B2 | 9/2009 | Wasielewski | |
| 7,632,283 B2 | 12/2009 | Heldreth | |
| 7,632,314 B2 | 12/2009 | Dietz | |
| 7,695,520 B2 | 4/2010 | Metzger et al. | |
| 7,837,691 B2 | 11/2010 | Cordes et al. | |
| 7,850,698 B2 | 12/2010 | Straszheim-Morley et al. | |
| 8,065,927 B2 | 11/2011 | Crottet et al. | |
| 8,141,437 B2 | 3/2012 | Amirouche et al. | |
| 8,197,549 B2 | 6/2012 | Amirouche et al. | |
| 8,211,041 B2 | 7/2012 | Fisher et al. | |
| 8,245,583 B2 | 8/2012 | Stein | |
| 8,491,589 B2 | 7/2013 | Fisher et al. | |
| 8,506,571 B2 | 8/2013 | Chana et al. | |
| 8,603,101 B2 | 12/2013 | Claypool et al. | |
| 9,011,459 B2 | 4/2015 | Claypool et al. | |
| 9,149,206 B2 | 10/2015 | Claypool et al. | |
| 2002/0058997 A1 | 5/2002 | O'Connor et al. | |
| 2002/0072802 A1 | 6/2002 | O'Neil et al. | |
| 2004/0019382 A1 | 1/2004 | Amirouche et al. | |
| 2004/0064191 A1 | 4/2004 | Wasielewski | |
| 2004/0167537 A1 | 8/2004 | Errico et al. | |
| 2004/0225368 A1 | 11/2004 | Plumet et al. | |
| 2005/0055102 A1 | 3/2005 | Tornier et al. | |
| 2005/0177170 A1 | 8/2005 | Fisher et al. | |
| 2005/0267485 A1 | 12/2005 | Cordes et al. | |
| 2006/0020343 A1 | 1/2006 | Ek | |
| 2006/0052782 A1 | 3/2006 | Morgan et al. | |
| 2006/0069436 A1 | 3/2006 | Sutton et al. | |
| 2006/0184176 A1 | 8/2006 | Straszheim-Morley et al. | |
| 2006/0189864 A1* | 8/2006 | Paradis | A61B 19/52 600/407 |
| 2006/0190087 A1 | 8/2006 | O'Connor et al. | |
| 2006/0239922 A1 | 10/2006 | Cooper | |
| 2007/0123992 A1 | 5/2007 | Sanford | |
| 2007/0234819 A1 | 10/2007 | Amirouche et al. | |
| 2007/0239165 A1 | 10/2007 | Amirouche | |
| 2008/0051908 A1 | 2/2008 | Angibaud et al. | |
| 2008/0091273 A1 | 4/2008 | Hazebrouck | |
| 2008/0103603 A1 | 5/2008 | Hintermann | |
| 2009/0005708 A1 | 1/2009 | Johanson et al. | |
| 2009/0125114 A1 | 5/2009 | May et al. | |
| 2009/0204222 A1 | 8/2009 | Burstein et al. | |
| 2009/0259314 A1 | 10/2009 | Linder-Ganz et al. | |
| 2009/0264894 A1* | 10/2009 | Wasielewski | A61B 19/46 606/102 |
| 2009/0287310 A1 | 11/2009 | Fisher et al. | |
| 2009/0306787 A1 | 12/2009 | Crabtree et al. | |
| 2010/0010494 A1 | 1/2010 | Quirno | |
| 2010/0063595 A1 | 3/2010 | Dietz | |
| 2010/0076563 A1 | 3/2010 | Otto et al. | |
| 2010/0082111 A1 | 4/2010 | Thomas | |
| 2010/0100011 A1 | 4/2010 | Roche | |
| 2010/0198275 A1 | 8/2010 | Chana et al. | |
| 2010/0249660 A1* | 9/2010 | Sherman | A61B 19/46 600/587 |
| 2010/0249789 A1 | 9/2010 | Rock et al. | |
| 2011/0100011 A1 | 5/2011 | Staffend | |
| 2012/0095563 A1 | 4/2012 | Sanford et al. | |
| 2012/0158152 A1 | 6/2012 | Claypool et al. | |
| 2012/0179069 A1 | 7/2012 | Amirouche | |
| 2012/0232429 A1 | 9/2012 | Fischer et al. | |
| 2012/0290088 A1 | 11/2012 | Amirouche et al. | |
| 2012/0310246 A1 | 12/2012 | Belcher et al. | |
| 2013/0013076 A1 | 1/2013 | Fisher et al. | |
| 2013/0079671 A1 | 3/2013 | Stein et al. | |
| 2013/0096567 A1 | 4/2013 | Fisher et al. | |
| 2013/0102929 A1 | 4/2013 | Haight et al. | |
| 2013/0103038 A1 | 4/2013 | Fischer et al. | |
| 2013/0261504 A1 | 10/2013 | Claypool et al. | |
| 2013/0261757 A1 | 10/2013 | Claypool et al. | |
| 2013/0261758 A1 | 10/2013 | Claypool et al. | |
| 2014/0052269 A1 | 2/2014 | Claypool et al. | |
| 2014/0296859 A1 | 10/2014 | Claypool et al. | |
| 2015/0190243 A1 | 7/2015 | Claypool et al. | |
| 2015/0359642 A1 | 12/2015 | Claypool et al. | |

FOREIGN PATENT DOCUMENTS

| | | |
|---|---|---|
| CN | 101522136 A | 9/2009 |
| CN | 101711701 A | 5/2010 |
| CN | 101835441 A | 9/2010 |
| CN | 102018584 A | 4/2011 |
| CN | 103370025 A | 10/2013 |
| CN | 103379880 A | 10/2013 |
| CN | 104379094 A | 2/2015 |
| CN | 104736105 A | 6/2015 |
| CN | 105055052 A | 11/2015 |
| EP | 0903125 A1 | 3/1999 |
| EP | 1132063 A2 | 9/2009 |
| EP | 2237177 A1 | 10/2010 |
| EP | 2830543 A1 | 2/2015 |
| EP | 2830544 A1 | 2/2015 |
| FR | 2824260 A1 | 11/2002 |
| JP | 61247449 A | 11/1986 |
| JP | 09289998 A | 11/1997 |
| JP | 2007054488 A | 3/2007 |
| JP | 2009245619 A | 10/2009 |
| JP | 20120240406 A | 10/2010 |
| JP | 2015512307 A | 4/2013 |
| JP | 2014505517 A | 3/2014 |
| JP | 2014508554 A | 4/2014 |
| JP | 2014239900 A | 12/2014 |
| JP | 2015513966 A | 5/2015 |
| WO | WO-2010022272 A1 | 2/2010 |
| WO | WO-2010023062 A2 | 3/2010 |
| WO | WO-2011063123 A2 | 5/2011 |
| WO | WO-2012004580 A1 | 1/2012 |
| WO | WO-2012020460 A1 | 2/2012 |

(56) References Cited

FOREIGN PATENT DOCUMENTS

| WO | WO-2012082628 A1 | 6/2012 |
|---|---|---|
| WO | WO-2013148954 A1 | 10/2013 |
| WO | WO-2013148960 A1 | 10/2013 |

OTHER PUBLICATIONS

"U.S. Appl. No. 13/836,665, Examiner Interview Summary mailed Jul. 17, 2014", 4 pgs.
"U.S. Appl. No. 13/836,665, Final Office Action mailed Jul. 25, 2014", 25 pgs.
"U.S. Appl. No. 13/836,665, Response filed May 30, 2014 to Non-Final Office Action mailed Jan. 30, 2014", 21 pgs.
"U.S. Appl. No. 13/837,774, Examiner Interview Summary mailed Jul. 22, 2014", 4 pgs.
"U.S. Appl. No. 13/837,774, Final Office Action mailed Jul. 28, 2014", 17 pgs.
"U.S. Appl. No. 13/837,774, Response filed Jun. 10, 2014 to Non-Final Office Action mailed Feb. 20, 2014", 29 pgs.
"U.S. Appl. No. 14/063,032, Non Final Office Action mailed Jun. 20, 2014", 6 pgs.
"U.S. Appl. No. 14/063,032, Notice of Allowance mailed Dec. 19, 2014", 6 pgs.
"U.S. Appl. No. 14/063,032, Response filed Oct. 20, 2014 to Non-Final Office Action mailed Jun. 20, 2014", 9 pgs.
"U.S. Appl. No. 14/304,009, Preliminary Amendment Filed Jul. 31, 2014", 7 pgs.
"Canadian Application Serial No. 2,824,527, Office Action mailed Mar. 17, 2014", 2 pgs.
"Canadian Application Serial No. 2,824,527, Response filed Sep. 17, 2014 to Office Action mailed Mar. 17, 2014", 14 pgs.
"Chinese Application Serial No. 201180067430.X, Office Action mailed Aug. 28, 2014", (With English Translation), 8 pgs.
"International Application Serial No. PCT/US2013/034286, International Preliminary Report on Patentability mailed Oct. 9, 2014", 8 pgs.
"International Application Serial No. PCT/US2013/034293, International Preliminary Report on Patentability mailed Oct. 9, 2014", 9 pgs.
"Japanese Application Serial No. 2013-544858, Request for Examination filed Feb. 4, 2014", (With English Translation), 14 pgs.
"U.S. Appl. No. 13/836,665, Response filed Jan. 23, 2015 to Final Office Action mailed Jul. 25, 2014", 25 pgs.
"U.S. Appl. No. 13/837,774, Response filed Jan. 28, 2015 to Final Office Action mailed Jul. 28, 2014", 16 pgs.
"U.S. Appl. No. 14/660,217, Preliminary Amendment filed Mar. 18, 2015", 9 pgs.
"Chinese Application Serial No. 201180067430.X, Response filed Jan. 4, 2015 to Office Action mailed Sep. 26, 2014", (W/ English Translation), 14 pgs.
"European Application Serial No. 11808493.8, Examination Notification Art. 94(3) mailed Feb. 20, 2015", 6 pgs.
"U.S. Appl. No. 13/836,665, Non Final Office Action mailed Jan. 30, 2014", 21 pgs.
"U.S. Appl. No. 13/837,774, Non Final Office Action mailed Feb. 10, 2014", 33 pgs.
"U.S. Appl. No. 14/063,032, Preliminary Amendment filed Oct. 25, 2013", 3 pgs.
"Australian Application Serial No. 2011343440, First Examiner Report mailed Feb. 17, 2014", 3 pgs.
"Australian Application Serial No. 2011343440, Response filed Mar. 21, 2014 to Office Action mailed Feb. 17, 2014", 1 pg.
"Canadian Application Serial No. 2,821,927, Voluntary Amendment mailed Jun. 14, 2013", 7 pgs.
"Chinese Application Serial No. 201180067757.7, Voluntary Amendment mailed Feb. 14, 2014", 4 pgs.
"U.S. Appl. No. 13/087,610, Non Final Office Action mailed Feb. 26, 2013", 7 pgs.

"U.S. Appl. No. 13/087,610, Notice of Allowance mailed Jun. 28, 2013", 6 pgs.
"U.S. Appl. No. 13/087,610, Notice of Allowance mailed Oct. 8, 2013", 7 pgs.
"U.S. Appl. No. 13/087,610, Response filed May 24, 2013 to Non Final Office Action mailed Feb. 26, 2013", 15 pgs.
"International Application Serial No. PCT/US2011/064435, International Preliminary Report on Patentability mailed Jun. 27, 2013", 9 pgs.
"International Application Serial No. PCT/US2011/064435, Written Opinion mailed Jun. 21, 2012", 7 pgs.
"International Application Serial No. PCT/US2011/065683, International Preliminary Report on Patentability mailed Jun. 27, 2013", 11 pgs.
"International Application Serial No. PCT/US2013/034286, International Search Report mailed Jun. 25, 2013", 6 pgs.
"International Application Serial No. PCT/US2013/034286, Written Opinion mailed Jun. 25, 2013", 6 pgs.
"International Application Serial No. PCT/US2013/034293, International Search Report mailed Jun. 25, 2013", 6 pgs.
"International Application Serial No. PCT/US2013/034293, Written Opinion mailed Jun. 25, 2013", 7 pgs.
U.S. Appl. No. 13/836,665, filed Mar. 15, 2013, Tibial Prosthesis Systems, Kits, and Methods.
U.S. Appl. No. 13/837,294, filed Mar. 15, 2013, Tibial Prosthesis Systems, Kits, and Methods.
U.S. Appl. No. 13/837,774, filed Mar. 15, 2013, Tibial Prosthesis Systems, Kits, and Methods.
U.S. Appl. No. 14/063,032, filed Oct. 25, 2013, Provisional Tibial Prosthesis System.
"International Application Serial No. PCT/US2011/064435, Search Report mailed Jun. 21, 2012", 5 pgs.
"International Application Serial No. PCT/US2011/065683, International Search Report mailed Apr. 24, 2012", 12 pgs.
"International Application Serial No. PCT/US2011/065683, Written Opinion mailed Apr. 24, 2012", 10 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
"U.S. Appl. No. 13/836,665, Notice of Allowance mailed Jun. 9, 2015", 10 pgs.
"U.S. Appl. No. 13/837,774, Response filed Jul. 7, 2015 to Restriction Requirement mailed May 20, 2015", 10 pgs.
"U.S. Appl. No. 13/837,774, Restriction Requirement mailed May 20, 2015", 6 pgs.
"Chinese Application Serial No. 201180067757.7, Office Action mailed Mar. 2, 2015", W/ English Translation, 18 pgs.
"Japanese Application Serial No. 2014-121515, Office Action mailed Jun. 2, 2015", (W/ English Translation), 10 pgs.
"U.S. Appl. No. 13/837,294, Non Final Office Action mailed Dec. 10, 2015", 8 pgs.
"U.S. Appl. No. 13/837,294, Response filed Oct. 12, 2015 to Restriction Requirement mailed Aug. 24, 2015", 9 pgs.
"U.S. Appl. No. 13/837,294, Restriction Requirement mailed Aug. 24, 2015"6 pgs.
"U.S. Appl. No. 13/837,774, Non Final Office Action mailed Sep. 18, 2015", 16 pgs.
"U.S. Appl. No. 13/837,774, Response filed Dec. 16, 2015 to Non Final Office Action mailed Sep. 18, 2015", 17 pgs.
"U.S. Appl. No. 14/660,217, Non Final Office Action mailed Dec. 17, 2015", 8 pgs.
"U.S. Appl. No. 14/833,385, Preliminary Amendment filed Aug. 25, 2015", 6 pgs.
"Chinese Application Serial No. 201180067757.7, Office Action mailed Nov. 16, 2015", (W/ English Translation), 17 pgs.
"Chinese Application Serial No. 201180067757.7, Response filed Jul. 10, 2015 to Office Action mailed Mar. 2, 2015", (W/ English Translation), 13 pgs.
"Chinese Application Serial No. 201380028572.4, Office Action mailed Aug. 13, 2015", (W/ English Translation), 16 pgs.
"Chinese Application Serial No. 201380028683.5, Office Action mailed Nov. 4, 2015", W/ English Translation, 16 pgs.

(56) References Cited

OTHER PUBLICATIONS

"European Application Serial No. 13716636.9, Communication Pursuant to Article 94(3) EPC mailed Nov. 16, 2015", 4 pgs.

"European Application Serial No. 13716636.9, Communication pursuant to Rules 161(1) and 162 EPC mailed Dec. 12, 2014", 2 pgs.

"European Application Serial No. 13716636.9, Response filed Jun. 22, 2015 to Communication pursuant to Rules 161(1) and 162 EPC mailed Dec. 12, 2014", 10 pgs.

"European Application Serial No. 14190180.1, Extended European Search Report mailed Sep. 24, 2015", 8 pgs.

"Japanese Application Serial No. 2013-544655, Office Action mailed Sep. 29, 2015", (W/ English Translation), 7 pgs.

U.S. Appl. No. 14/833,385, filed Aug. 24, 2015, Tibial Prosthesis Systems, Kits, and Methods.

U.S. Appl. No. 14/660,217, filed Mar. 17, 2015, Provisional Tibial Prosthesis System.

"U.S. Appl. No. 13/837,294, Final Office Action mailed Apr. 25, 2016", 7 pgs.

"U.S. Appl. No. 13/837,294, Response filed Mar. 4, 2016 to Non Final Office Action mailed Dec. 10, 2015", 16 pgs.

"U.S. Appl. No. 13/837,774, Final Office Action mailed Mar. 17, 2016", 14 pgs.

"U.S. Appl. No. 14/660,217, Notice of Allowance mailed Apr. 26, 2016", 5 pgs.

"U.S. Appl. No. 14/660,217, Response filed Mar. 23, 2016 to Non Final Office Action mailed Dec. 17, 2015", 14 pgs.

"Australian Application Serial No. 2013238046, First Examiner Report mailed Nov. 26, 2015", 2 pgs.

"Australian Application Serial No. 2013238046, Response filed Feb. 2, 2016 to First Examiner Report mailed Nov. 26, 2015", 1 pg.

"Chinese Application Serial No. 201180067757.7, Response filed Jan. 27, 2016 to Office Action mailed Nov. 16, 2015", (W/ English Translation of Claims), 12 pgs.

"Chinese Application Serial No. 201380028683.5, Response filed Mar. 18, 2016 to Office Action mailed Nov. 4, 2015", (W/ English Translation of Claims), 11 pgs.

"Japanese Application Serial No. 2013-544655, Office Action mailed Mar. 8, 2016", (W/ English Translation), 8 pgs.

"Japanese Application Serial No. 2013-544655, Response filed Jan. 4, 2016 to Office Action mailed Sep. 29, 2015", (English Translation of Claims), 14 pgs.

"Japanese Application Serial No. 2014-121515, Notice of Reasons for Rejection mailed Jan. 5, 2016", (W/ English Translation), 9 pgs.

* cited by examiner

USER INTERFACE RELATED TO A SURGICAL PROVISIONAL

RELATED APPLICATION

This patent document is a U.S. National Stage Filing under 35 U.S.C. §371 of International Patent Application Serial No. PCT/US2011/064435, filed on Dec. 12, 2011, published on Jun. 21, 2012 as WO 2012/082628 A1, and entitled "USER INTERFACE RELATED TO A SURGICAL PROVISIONAL," which claims the benefit of priority under 35 U.S.C. §119(e) of U.S. Provisional Application Ser. No. 61/424,222, filed on Dec. 17, 2010, entitled "USER INTERFACE RELATED TO A SURGICAL PROVISIONAL," the benefit of priority of each of which is claimed hereby and each of which is incorporated by reference herein in its entirety.

BACKGROUND AND SUMMARY

The present disclosure relates generally to orthopedic devices and in particular to orthopedic devices including sensors and a user interface of a computing device associated with the orthopedic device.

In a knee replacement procedure, a provisional device may be inserted in the joint to assist in determining the size of tibia implant to use. A height of the provisional device may be increased with shims.

In an exemplary embodiment of the present disclosure, a user interface generated with a computing device by instructions stored on at least one computer-readable medium is provided. The user interface presenting on a display objects related to a knee joint. At least one of the objects being based on data from a plurality of sensors which are located between the femur and the tibia. The user interface comprising a representation of an area of the knee joint for presentment on the display; and a force center indicator for presentment on the display. The user interface providing an indication of when a position of the force center indicator corresponds to a desired position of the force center indicator. The position of the force center indicator being determined by an electronic controller of the computing device based on data from the plurality of sensors.

In another exemplary embodiment of the present disclosure, a user interface generated with a computing device by instructions stored on at least one computer-readable medium is provided. The user interface presenting objects on a display related to a knee joint. At least one of the objects being based on data from a plurality of sensors which are located between the femur and the tibia and supported by a device having a posterior ridge. The user interface comprising a representation of an area of the knee joint for presentment on the display; and at least one indicator for presentment on the display, the at least one indicator indicating a force level on the posterior ridge of the device. The force level on the posterior ridge being determined by an electronic controller of the computing device based on data from the plurality of sensors.

In yet another exemplary embodiment of the present disclosure, a user interface generated with a computing device by instructions stored on at least one computer-readable medium is provided. The user interface presenting objects on a display related to a knee joint. At least one of the objects being based on data from a plurality of sensors which are located between the femur and the tibia. The user interface comprising a representation of an area of the knee joint for presentment on the display; an overall force center indicator for presentment on the display relative to the representation; a medial force center indicator for presentment on the display relative to the representation; and a lateral force center indicator for presentment on the display relative to the representation, a position of the overall force center indicator, a position of the medial force center indicator, and a position of the lateral force center indicator being determined by an electronic controller of the computing device based on data from the plurality of sensors.

In still another exemplary embodiment of the present disclosure, a user interface generated with a computing device by instructions stored on at least one computer-readable medium is provided. The user interface presenting objects on a display related to a knee joint. At least one of the objects being based on data from a plurality of sensors which are located between the femur and the tibia. The user interface comprising a representation of an area of the knee joint for presentment on the display; and at least one indicator for presentment on the display, the at least one indicator indicating a force level on a post of the device which is received in a recess in one of the femur and the tibia, the force level on the post being determined by an electronic controller of the computing device based on data from the plurality of sensors.

In a further exemplary embodiment of the present disclosure, a user interface generated with a computing device by instructions stored on at least one computer-readable medium is provided. The user interface presenting objects on a display related to a knee joint. At least one of the objects being based on data from a plurality of sensors which are located between the femur and the tibia. The user interface comprising a representation of an area of the knee joint for presentment on the display; a force center indicator for presentment on the display; and a spread force indicator for presentment on the display. The spread force indicator providing an indication of a spread of the forces across the area of the knee joint. The position of the force center indicator and the spread force indicator being determined by an electronic controller of the computing device based on data from the plurality of sensors.

In a yet further exemplary embodiment of the present disclosure, a user interface generated with a computing device by instructions stored on at least one computer-readable medium is provided. The user interface presenting objects on a display related to a knee joint. At least one of the objects being based on data from a plurality of sensors which are located between the femur and the tibia. The user interface comprising a representation of an area of the knee joint for presentment on the display; and a force center indicator for presentment on the display. The user interface providing an indication of a first position of the force center indicator when the knee joint is in a first position and of a second position of the force center indicator when the knee joint is in a second position. The first position of the force center indicator and the second position of the force center indicator being determined by an electronic controller of the computing device based on data from the plurality of sensors.

In a still further exemplary embodiment of the present disclosure, a user interface generated with a computing device by instructions stored on at least one computer-readable medium is provided. The user interface for presenting objects on a display related to a knee joint. At least one of the objects being based on data from a plurality of sensors which are located between the femur and the tibia. The user interface comprising a representation of an area of the knee joint for presentment on the display; and a force center indicator for presentment on the display. The user interface providing an indication of a first position of the force center indicator when the knee joint is in a first position and of a second position of the force center indicator when the knee joint is in the first position. The first position of the force center indicator corresponding to a first environment for the knee joint and the second position of the force center indicator corresponding to a second environment of the knee joint. The first position of the force center indicator and the second position of the force center indicator being determined by an electronic controller of the computing device based on data from the plurality of sensors.

In a yet still further exemplary embodiment of the present disclosure, a system for evaluating a knee joint is provided. The system comprising a provisional selected from a plurality of provisionals, the provisional including a plurality of sensors which are located between the femur and the tibia when the provisional is positioned in the knee joint; and a computing system including a display. The computing system executes a processing sequence to identify the provisional and presents a user interface on the display to provide an indication of the force experienced by the plurality of sensors.

In still yet another exemplary embodiment of the present disclosure, a user interface generated with a computing device by instructions stored on at least one computer-readable medium is provided. The user interface presenting objects on a display related to a simulation of a knee joint. The user interface comprising at least one input to specify force readings across an area of the knee joint; and a force center indicator for presentment on the display. The user interface providing an indication of a position of the force center indicator relative to a desired position of the force center indicator, the position of the force center indicator being determined by an electronic controller of the computing device based on the specified force readings across the area of the knee joint.

In still a further exemplary embodiment of the present disclosure, a user interface generated with a computing device by instructions stored on at least one computer-readable medium is provided. The user interface presenting objects on a display related to a simulation of a knee joint. The user interface comprising at least one input to specify simulation force readings across an area of the knee joint, each force reading corresponding to a respective sensor of a provisional; and at least one visual indicator for presentment on the display, the at least one visual indicator providing a visual cue of the force experienced by the provisional based on the simulation force readings.

In yet still another exemplary embodiment of the present disclosure, a method of analyzing forces on a provisional placed in a knee joint is provided. The method comprising the steps of receiving from the provisional information related to the provisional, the provisional including a plurality of sensors, the information related to the provisional including at least one of identifying information for the provisional, location information of the plurality of sensors of the provisional, and a visual representation of the provisional; electronically receiving from the provisional information related to a force experienced by the plurality of sensors of the provisional; and determining at least one measure of the force experienced by the provisional from the information related to the force experienced by the plurality of sensors.

BRIEF DESCRIPTION OF THE DRAWINGS

The foregoing aspects and many of the attendant advantages of this invention will become more readily appreciated as the same become better understood by reference to the following detailed description when taken in conjunction with the accompanying drawings.

Figure 1:
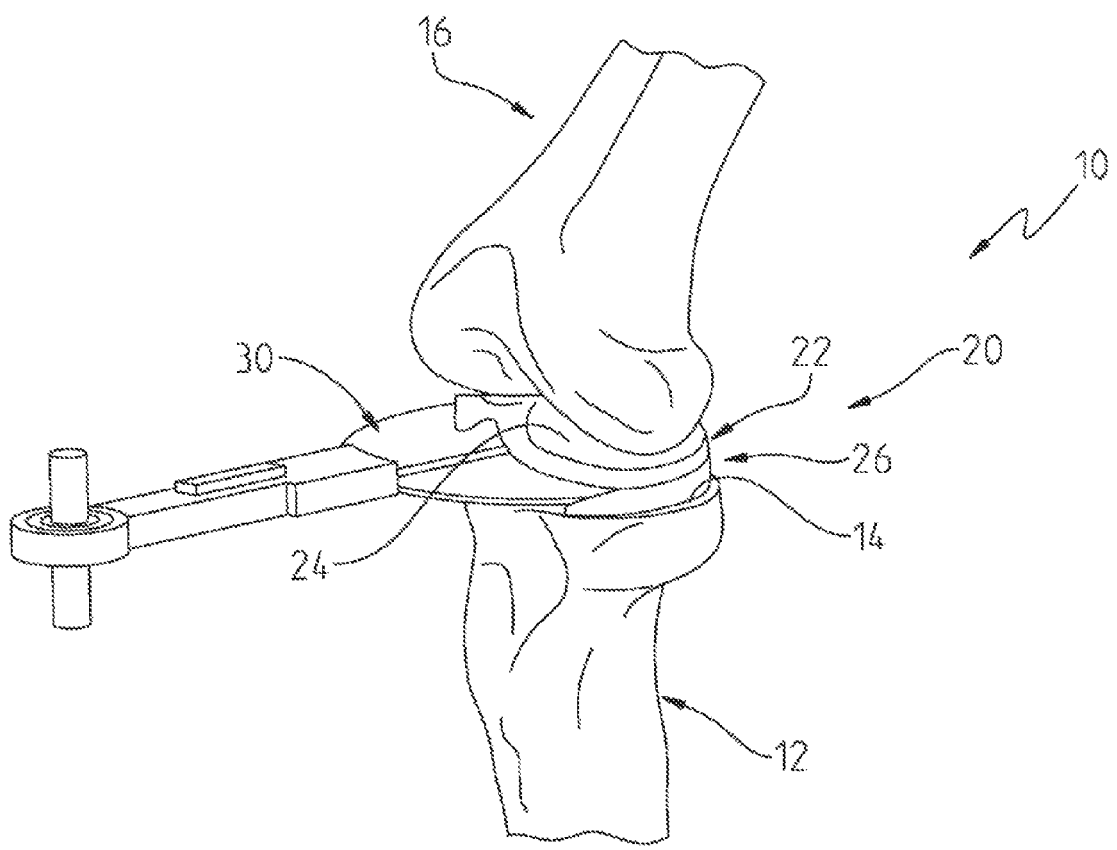
FIG. 1 is a representative view of an exemplary knee joint being evaluated with a sensing provisional.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates embodiments of the invention, and such exemplifications are not to be construed as limiting the scope of the invention in any manner.

DETAILED DESCRIPTION OF THE DRAWINGS

For the purposes of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

Referring to FIG. 1, a knee joint 10 is represented. The knee joint 10 includes a tibia bone 12 which has been resected to provide a resection surface 14. The knee joint 10 further includes a femur bone 16. A provisional 20 is shown being inserted between femur 16 and resection surface 14 of tibia 12 to simulate the fit of an implant in the knee joint 10.

Provisional 20 includes an upper portion 22 having a contoured top surface 24 which corresponds to the tibial articular surface of the implant to be used. Provisional 20 further includes a base portion 26 which rests upon resection surface 14 of tibia 12. The fit of provisional 20 in tibia 12 may be adjusted by inserting one or more shims 30 between upper portion 22 and base portion 26 to adjust spacing between upper portion 22 and base portion 26.

Figure 2:
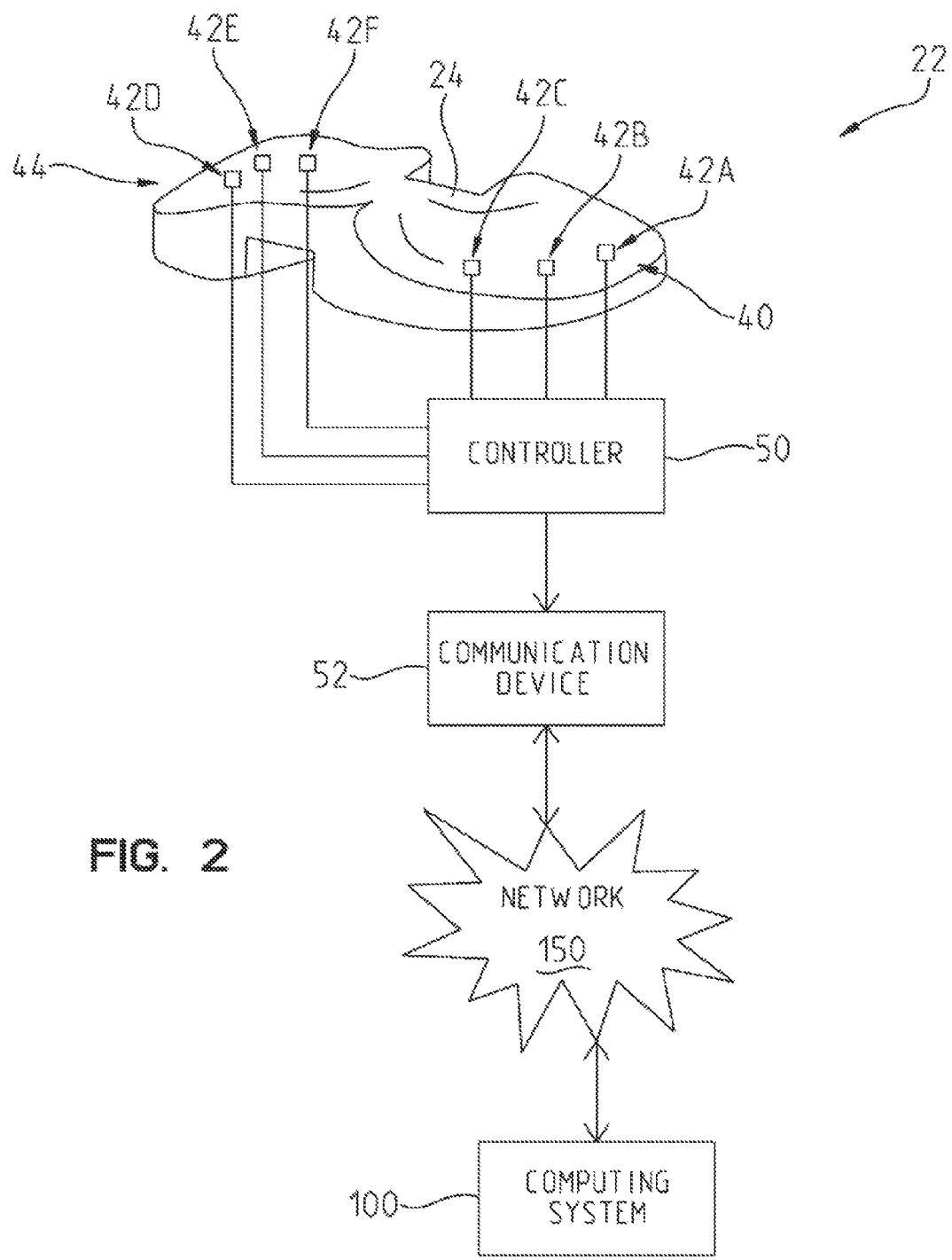
FIG. 2 is a representative view of a portion of the sensing provisional of FIG. 1.

Referring to FIG. 2, upper portion 22 includes a plurality of force sensors positioned below contoured top surface 24. In one embodiment, the force sensors are embedded in upper portion 22. In the illustrated embodiment, upper portion 22 includes a first group 40 of force sensors, illustratively sensors 42A-C, and a second group 44 of force sensors, illustratively sensors 42D-F. Exemplary force sensors include force sensing resistor or capacitive flex circuits, piezoelectric film, piezoelectric elements, piezoresistive and piezoelectric polymers, metal foil strain gages, semiconductor strain gages, piezoresistive and capacitive pressure sensors, interferometric optical sensors, path displacement optical sensors, optical fiber force sensors, and other suitable sensing technologies.

Each of force sensors 42 is operatively coupled to a controller 50 of provisional 20. Controller 50 receives or otherwise monitors an indication of the amount of force experienced by each of the force sensors 42. Controller 50 communicates the force data to remote computing system 100 through a communication device 52. An exemplary communication device 52 is a radio wave transmitter or other suitable devices for wirelessly transmitting information to a remote computing system 100. In one embodiment, the communication device further includes a receiver for receiving information from the remote computing system 100. In one embodiment, the controller 50 and the communication device 52 is supported by upper portion 22 of provisional 20.

In one embodiment, provisional 20 includes a unique data encoding which is stored in a memory associated with controller 50 and is provided through communication device 52 to computing system 100 to identify the provisional 20 being used. In one example, computing system 100 then queries a provisional database 120 to retrieve information regarding the identified provisional. In one example, provisional 20 through communication device 52 provides to computing system 100 information regarding the provisional 20. Exemplary information includes brand information, product line information, medial/lateral information, size information, poly thickness information, lot number, serial number, rendered images for use in the computing system graphical user interface, sensor configuration, calibration data, and other suitable information. This information may be used for recordation in a patient file, used for inventory management and traceability. Further, the information includes information for display with a display 132 of remote computing device 100 including specific provisional surface geometry, sensor layout, and degree of constraint. In one embodiment, the provisional data may be uploaded from provisional 20 to computing system 100 on activation and connection of the provisional 20 with the computing system 100.

In one embodiment, provisional 20 or its associated packaging includes visible identification information. Exemplary identification information may be provided in or determinable from a barcode. A camera associated with the computing device 100 captures an image including the identification information. In the case of a barcode, a scanner may be used in place of a camera. In one embodiment, the camera is integrated with the computing system 100. The identification information is extracted from the captured picture by computing system 100. Computing system 100 then broadcasts a unique identifier retrieved as part of or associated with the identification information as part of a wireless pairing protocol. Exemplary wireless pairing protocols include Bluetooth, Zigbee, and other protocols. The provisional 20 receives the broadcasted message and compares the broadcast unique identifier with a stored identifier. If the two match, the provisional 20 broadcasts its information to the computing system 100.

In one embodiment, provisional 20 broadcasts its unique identifier. The computing system 100 captures an image of identification information provided on the provisional or its packaging. If the unique identifier determined from the captured image corresponds to the unique identifier broadcasts by provisional 20, computing system 100 communicates with provisional 20.

In a similar fashion, each of shims 30 includes a unique data encoding which is provided through communication device 52 to computing system 100 to identify the shims 30 being used with provisional 20. In one embodiment, when a shim 30 is used with a provisional 20, the shim 30 is automatically detected by provisional 20 and information regarding the shim 30 is relayed to computing system 100 along with the sensor data of provisional 20. In one example, the identification is made via a set of hall effect sensors that form a bit pattern for controller 50. Each shim produces a unique bit pattern through an interaction with the hall effect sensors that is specific to the shim type or shim type combination. Other suitable methods of identification may be used.

In one example, computing system 100 queries a shim database 118 to retrieve information regarding the identified shim 30. In one example, provisional 20 through communication device 52 provides to computing system 100 information regarding the identified shim 30. Exemplary information includes brand information, product line information, thickness information, lot number, and other suitable information. This information may be used for recordation in a patient file to update thickness data and compensate algorithm calibrations accordingly, if necessary. In one embodiment, information regarding the identified shim is used in determining a joint angle. For example, if a joint angle is detected by computing system 100, the reported joint angle may be adjusted by the effective wedge angle of the shim combination, either in the anterior/posterior direction or the medial/lateral direction, as appropriate. The joint angle may be detected through the use of an integrated accelerometer, gyroscope, or combination of angular sensing devices, either internal or external to the provisional itself, or in combination with a corresponding angular sensing device attached to the femur.

In one embodiment, the information regarding the identified provisional 20 and the identified shims 30 is uploaded from provisional 20. Because all device specific data is uploaded from provisional 20, the application software of computing system 100 does not need to be upgraded to interface with a newly developed provisional 20 or shims 30.

Figure 3:
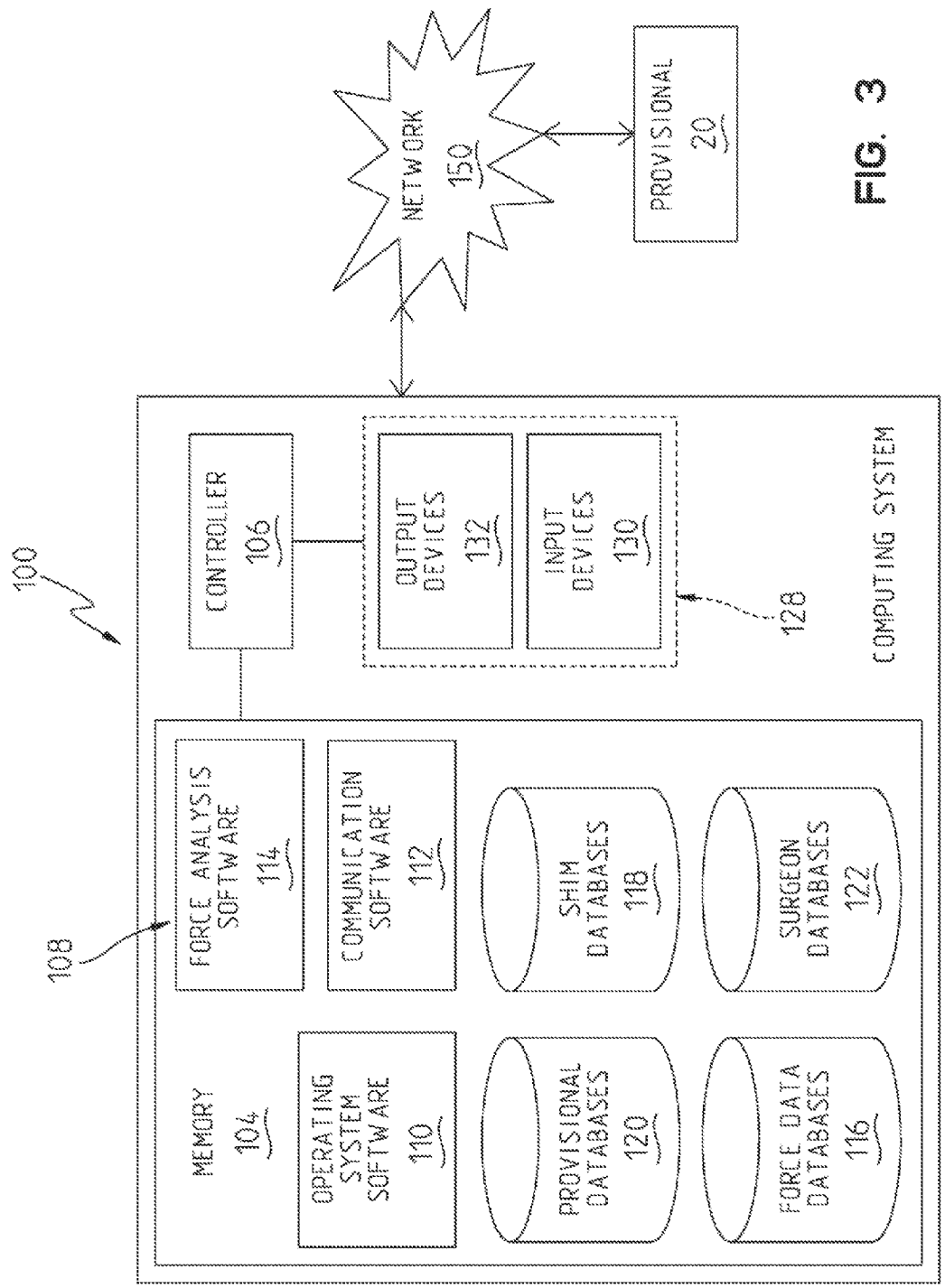
FIG. 3 is a representative view of an exemplary computing system including force analysis software related to the sensing provisional of FIG. 1 and a user interface.

Referring to FIG. 3, a computing system 100 is shown. Computing system 100 may be a stand alone computing device. Exemplary stand alone computing devices include a general purpose computer, such as a desktop computer, a laptop computer, and a tablet computer, smartphone, handheld computing device, or other suitable computing devices. An exemplary computing device is the IPAD brand computing device available from Apple Computer located 1 Infinite Loop in Cupertino, Calif. 95014. Although computing system 100 is illustrated as a single computing system, it should be understood that multiple computing systems may be used together, such as over a network or other methods of transferring data.

In one embodiment, computing system 100 is attached to the surgical table rails of a table supporting the patient, so that computing system 100 may be both physically small and within the immediate viewing space of the surgeon. In one embodiment, a display 132 of computing system 100 is a projected image. In one embodiment, a display 132 of computing system 100 is associated with the surgeon's glasses. In one embodiment, the computing system 100 or at least a display of computing system 100 is a handheld device intended to be held up by the circulating nurse for the surgeon to view only during the relevant portion of the procedure.

In one embodiment, interaction with a graphical user interface of computing system 100 is a touch screen or mechanical switches which are engaged by the surgeon or nurse. In one embodiment, the surgeon or nurse interacts with the computing system through voice commands received by a microphone associated with the computing system. In one example, the computing system is able to identify the voice of the surgeon or other authorized user. In one embodiment, the surgeon or nurse interacts with the computing system through gestures captured by a camera associated with the computing system. In any of the discussed embodiments, the computing system 100 or at least a display of the computing system 100 may be contained within a bag or other sterilization mechanism and the surgeon or other authorized user interacts with the computing system through the bag or other sterilization mechanism.

Computing system 100 has access to a memory 104 which is accessible by a controller 106 of computing system 100. Exemplary controllers include computer processors. Controller 106 executes software 108 stored on the memory 104. Memory 104 is a computer readable medium and may be a single storage device or may include multiple storage devices, located either locally with computing system 100 or accessible across a network. Computer-readable media may be any available media that may be accessed by controller 106 of computing system 100 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by computing system 100.

Memory 104 includes operating system software 110. An exemplary operating system software is a WINDOWS operating system available from Microsoft Corporation of Redmond, Wash. Memory 104 further includes communications software 112 which allows computing system 100 to communicate with one or more networks 150, such as a local area network, a wide area network, a public switched network, any type of wired network, any type of wireless network, and combinations thereof. An exemplary public switched network is the Internet. Exemplary communications software 112 includes browser software, and other types of software which permit computing system 100 to communicate with other devices across a network. In one embodiment, computing system 100 communicates with provisional 20 over an exemplary network 150. In one embodiment, computing system 100 also communicates with one or more additional computing devices over network 150, such as computing devices connected to a hospital network or surgery center network. In one embodiment, the software functions disclosed herein are implemented as hardware.

Memory 104 further includes force analysis software 114. Although described as software, it is understood that at least portions of the force analysis software 114 may, in some embodiments, be implemented as hardware.

As explained herein, force analysis software 114 receives an indication of the force measured by the sensors associated with provisional 20. Force analysis software 114 based on the measured force provides feedback for the operator through an output device 132 of a user interface 128, such as a display. Examples of the type feedback provided to the operator are disclosed herein and are illustrated in FIGS. 5-24.

Also, as explained herein, force analysis software 114 may reference one or more of at least one force data database 116, at least one shim database 118, at least one provisional database 120, and at least one surgeon database 122. Force analysis software 114 stores force readings for provisional 20 in force database 116. In one embodiment, the force readings for each sensor are stored and time-stamped in force database 116.

In one embodiment, shim database 118 includes information regarding a plurality of shims 30 that may be used with a provisional 20 and provisional database 120 includes information regarding a plurality of provisionals 20. In one example, provisional database 120 for a given provisional 20 includes a sensor layout and an image to represent the provisional 20 on a display 132. As mentioned herein, in one embodiment, the information regarding the identified provisional 20 and any identified shims 30 is uploaded from provisional 20 instead of being retrieved from provisional database 120 and shim database 118, respectively.

In one embodiment, computing system 100 further includes a surgeon database 122 which stores information related to a plurality of surgeons. In one embodiment, a surgeon logs on or is otherwise identified by computing system 100 and any preference information or other surgeon specific information in surgeon database 122 is retrieved. In one embodiment, the surgeon chooses to have force data displayed and/or interpreted relative to a historical set of case data from that surgeon. This information may be stored in the surgeon database or stored in the patient database. In another embodiment, the surgeon chooses to have force data displayed and/or interpreted relative to a historical set of case data from a different surgeon, a particular set of surgeons that the surgeon has identified, or the entire set of available case data from all surgeons. This information may be stored in the surgeon database or stored in the patient database. For example, if the surgeon desires to know if the knee is 'too tight' or 'too loose' in certain regions or in general, the surgeon may choose to have this indication be relative to the set of force readings that a particular set of surgeons, or the surgeon himself, have indicated as being 'too tight' or 'too loose' in previous cases. The surgeon may also choose to have feedback on the particular techniques that have been used by the surgeon or a defined set of surgeons in the past to handle clinical situations that closely match the sensor data for the surgeon's current case. Exemplary feedback includes providing an indication, such as a text message or graphical symbol, identifying a technique. Exemplary techniques include using a thicker shim, or pie-crusting a certain ligament.

Computing system 100 further includes a user interface 128. User interface 128 provides an interface for an operator to provide information to force analysis software 114 and to receive information from force analysis software 114. User interface 128 includes input devices 130 and output devices 132. Exemplary input devices 130 include a touch display, a keyboard, a mouse, one or more buttons or switches, a CD drive, a floppy drive, an interface to a network (wireless or wired), and other suitable devices for providing information to controller 106. Exemplary output devices 132 include a display (such as a touch screen), lights, printer, and other suitable devices for presenting information from controller 106.

In one embodiment, user interface 128 includes a graphical user interface through which an operator may provide information to force analysis software 114 with input devices 130 and receive information from force analysis software 114 through output devices 132.

Figure 4:
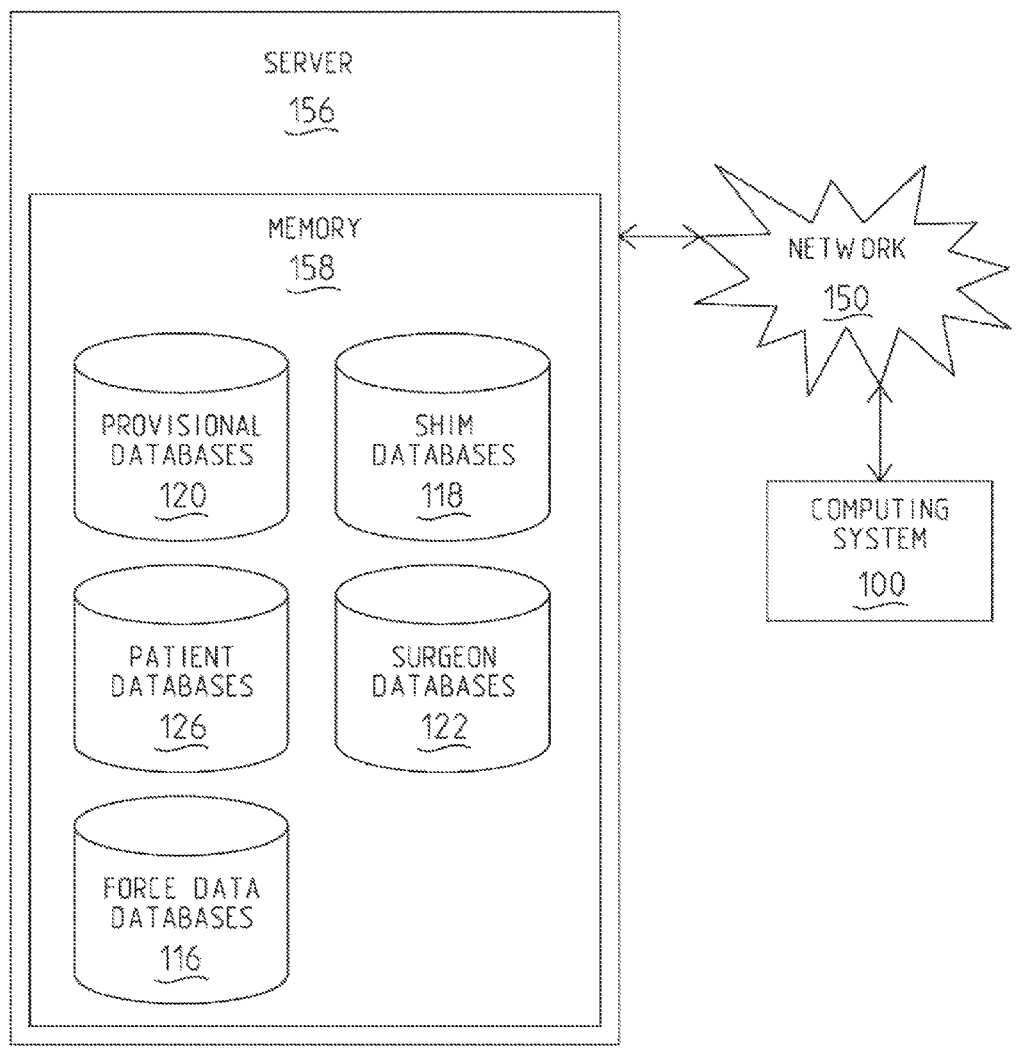
FIG. 4 is a representative view of a network accessible by the exemplary computing system of FIG. 3.

Referring to FIG. 4, in one embodiment, computing system 100 communicates with one or more other computing devices over a network 150, such as a server computer 156 associated with a hospital or surgical center. Network 150 may be any suitable connection between computing system 100 and server computer 156, such as a local area network, a wide area network, a wireless network, or other suitable networks. In one embodiment, network 150 utilizes the Internet for at least a portion of the connection between computing system 100 and server computer 156.

In one embodiment, force data database 116, shim database 118, provisional database 120, and surgeon database 122 are stored on a memory 158 accessible by server computer 156. By having force data database 116 located on memory 158, no patient specific data needs to be stored on computing system 100. In one embodiment, memory 158, includes a patient database 126 which stores the medical record information for a plurality of patients. The patient database may store information regarding the surgery being performed including force data related to provisional 20 and screenshots of the user interface portions provided on display 132.

Figure 5:
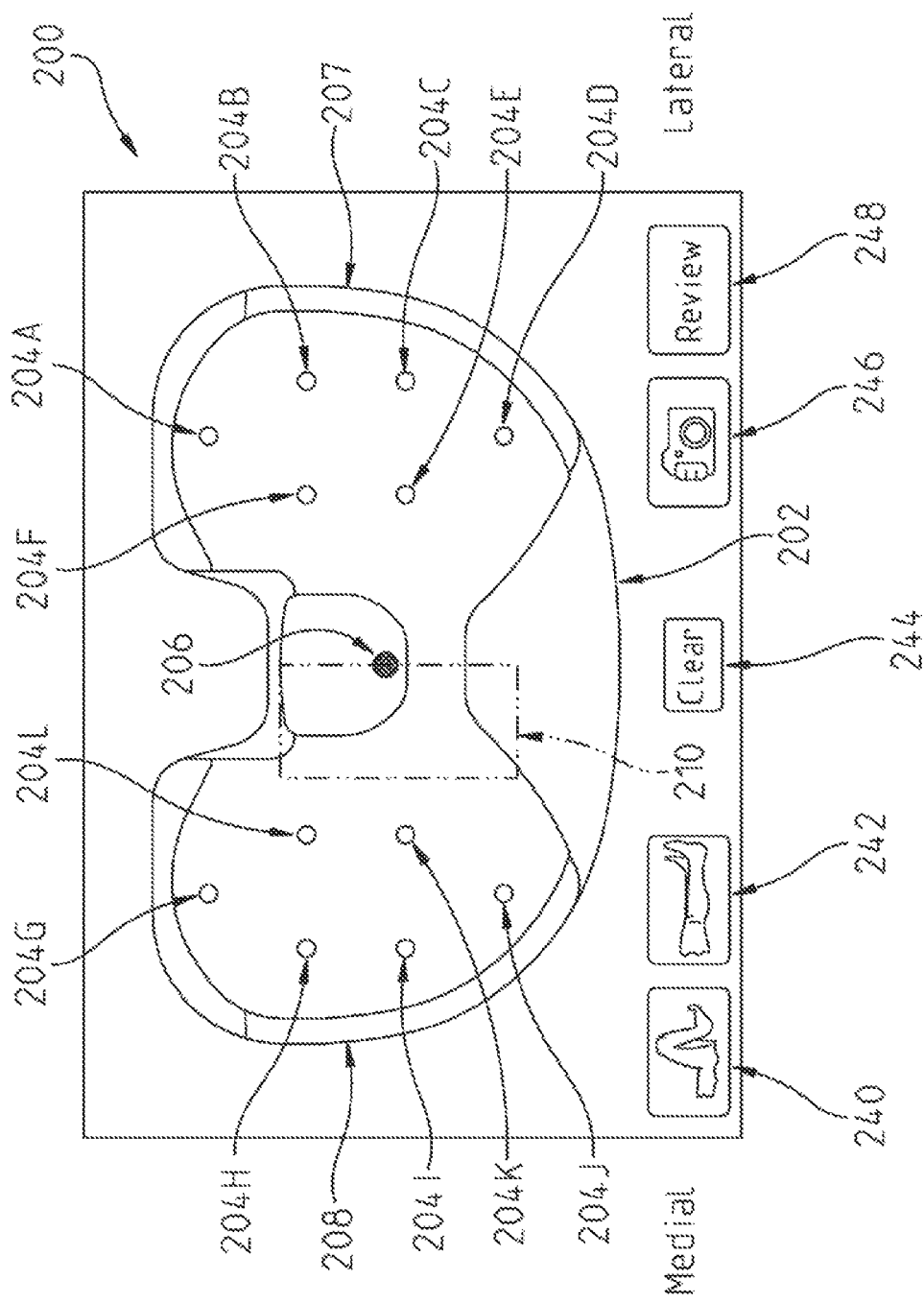
FIG. 5 is a representative view of an exemplary display screen of the user interface of the exemplary computing system of FIG. 3 including a representation of a force center indicator of the forces experienced by the sensing provisional of FIG. 1 and a representation of a desired location for the force center.

Referring to FIG. 5, an exemplary display screen 200 for user interface 128 is shown. Display screen 200 includes a provisional representation 202 of a top surface of provisional 20. Also shown on display screen 200 are sensor icons 204A-L indicating the location of each sensor 42 included in provisional 20. In the illustrated embodiment, provisional 20 includes twelve sensors 42. In the illustrated embodiment, a lateral compartment 207 of provisional 20 includes sensors 42A-F which correspond to sensor icon 204A-F and a medial compartment 208 of provisional 20 includes sensors 42G-L which correspond to sensors 204G-L.

The sensors 42 experience various levels of force from femur 16 when provisional 20 is inserted into knee joint 10. The force analysis software 114 based on the relative location of each of sensors 42 and the amount of force experienced by each sensor determines a location of a mean force applied from the femur on the tibia. The location of the mean force is represented in display screen 200 by a mean force center indicator 206. In one embodiment, mean force center indicator 206 is shown in a first color and sensors 204 are shown in a second color. In one example the first color is red and the second color is gold. In one embodiment, sensors icons 204 provide an indication of a level of force experienced by the respective sensor. Exemplary indications include color, color intensity, size, and other distinguishable features.

In the illustrated embodiment, display screen 200 also includes a bounded area 210. The bounded area 210 identifies an area in which the force delta would be considered small enough to result in a kinematically sound knee. The mean force center indicator 206 is shown partially overlapping bounded area 210. Therefore, the current force measurements result in a knee which is close to being considered kinematically sound. By adjusting provisional 20 with a shim 30, the location of mean force center indicator 206 may be altered. Further, by altering the ligaments of the knee the location of the mean force center indicator may be adjusted. An exemplary alteration is pie-crusting the ligaments.

Bounded area 210 is shown slightly medialized and being generally polygonal in shape. In one embodiment, the shape and location of bounded area 210 is settable by the user and stored in database 122. As such, a surgeon may establish their own custom bounded area 210. In one embodiment, the shape and location of bounded area 210 is set by the implant manufacturer. In one example, the shape and location of bounded area 210 is retrieved from a surgeon database 122 or provisional database 120 based on the sensor provisional being used.

In one embodiment, computing system 100 includes an audio interface as an exemplary output device 132. With the audio interface, a speaker may provide audio feedback to the surgeon so that the surgeon does not need to be looking at display screen 200 or display screen 220. Audio indications may be provided to indicate various device states to the surgeon while he is looking at the knee instead of the device display, and/or to provide additional confirmation of the visual indications. These audio indications may include confirmations of button presses, wireless connections being made or interrupted (alarm), the presence of the mean force center indicator 206 in bounded area 210 or region 268 (see FIG. 13A) via a variable or stepped frequency tone, or a variable frequency click (an exemplary variable frequency click is similar to Geiger Counter), the force sensors being saturated (force overload), the battery of provisional 20 running out, the sound of a photo being taken when selecting camera button 246, beeping noises when mean force center indicator 206 is moving, and other such indications.

In one embodiment, an audio only interface is provided to the user. In this case, computing system 100 may include recorded vocalized statements and instructions, for example.

Figure 6:
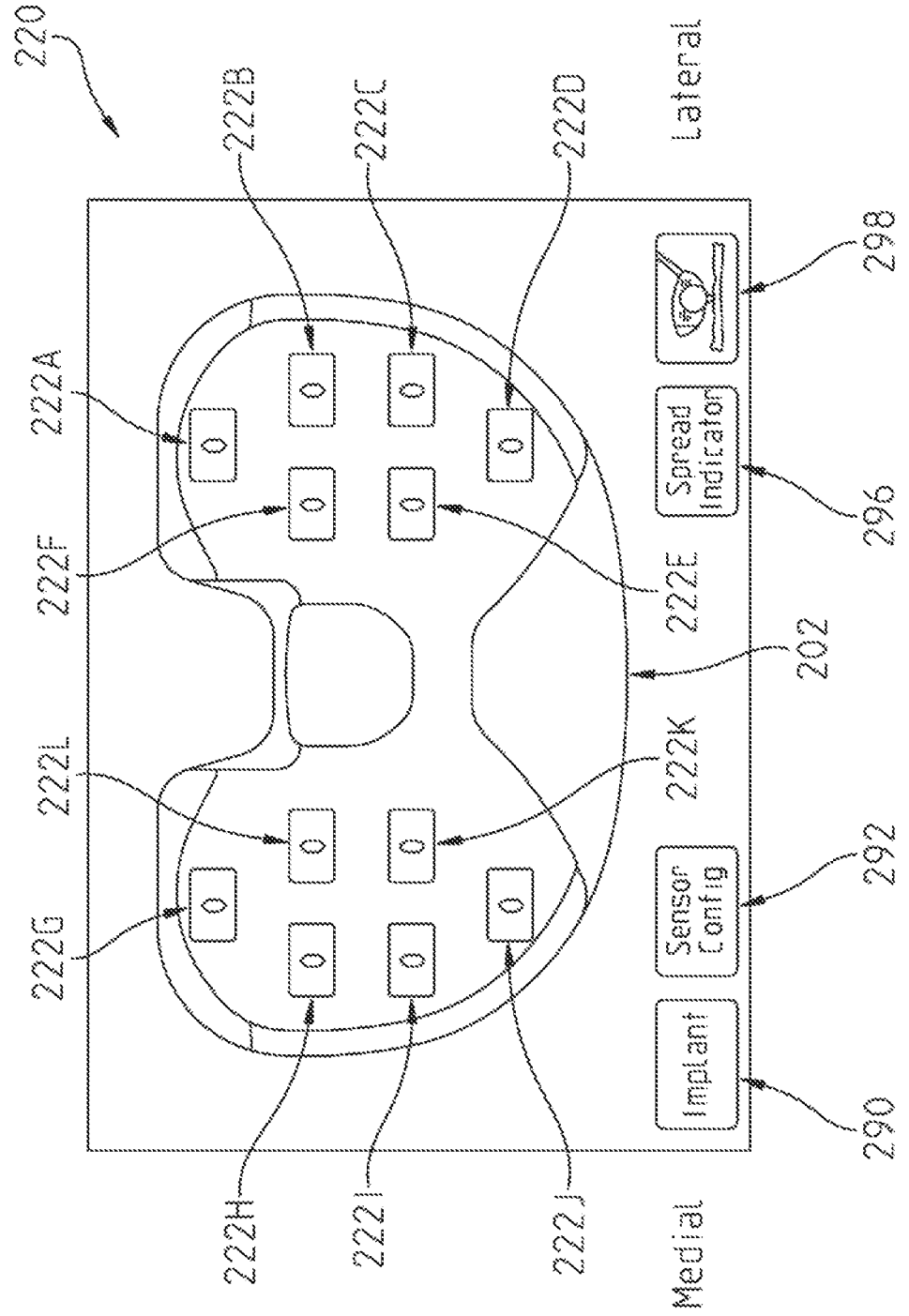
FIG. 6 is a representative view of another exemplary display screen of the user interface of FIG. 3 including representations of the force magnitude experienced by the sensors of the sensing provisional of FIG. 1 for FIG. 5.

Referring to FIG. 6, a second display screen 220 is shown. Display screen 220 includes provisional representation 202 and sensor icons 222A-L indicating both the location of each sensor 42 included in provisional 20 and a measure of the force reading of each sensor 42 included in provisional 20. In one embodiment, a value is provided on each sensor icons 222. In one embodiment, the value corresponding to each sensor icons 222 is the actual force measured by the respective force sensor. In one embodiment, the value corresponding to each sensor icons 222 is a normalized value of the force measured by the respective force sensor 42. In one embodiment, the value corresponding to each of sensor icons 222 indicates a range that the actual force of the force sensor falls within. For example, a "0" indicates generally no force; a "1" indicates a force within a first range of values; a "2" indicates a force within a second range of values, the second range of values being higher than the first range of values, and so on.

In one embodiment, the operator may change the force value assigned to a given icon 222 to see the effect on the mean force center indicator 206. In this embodiment, screen 200 and screen 220 are displayed at the same time. After a period of time or other input, the value of the icon 222 returns to the corresponding force experienced by the sensor.

Figure 7:
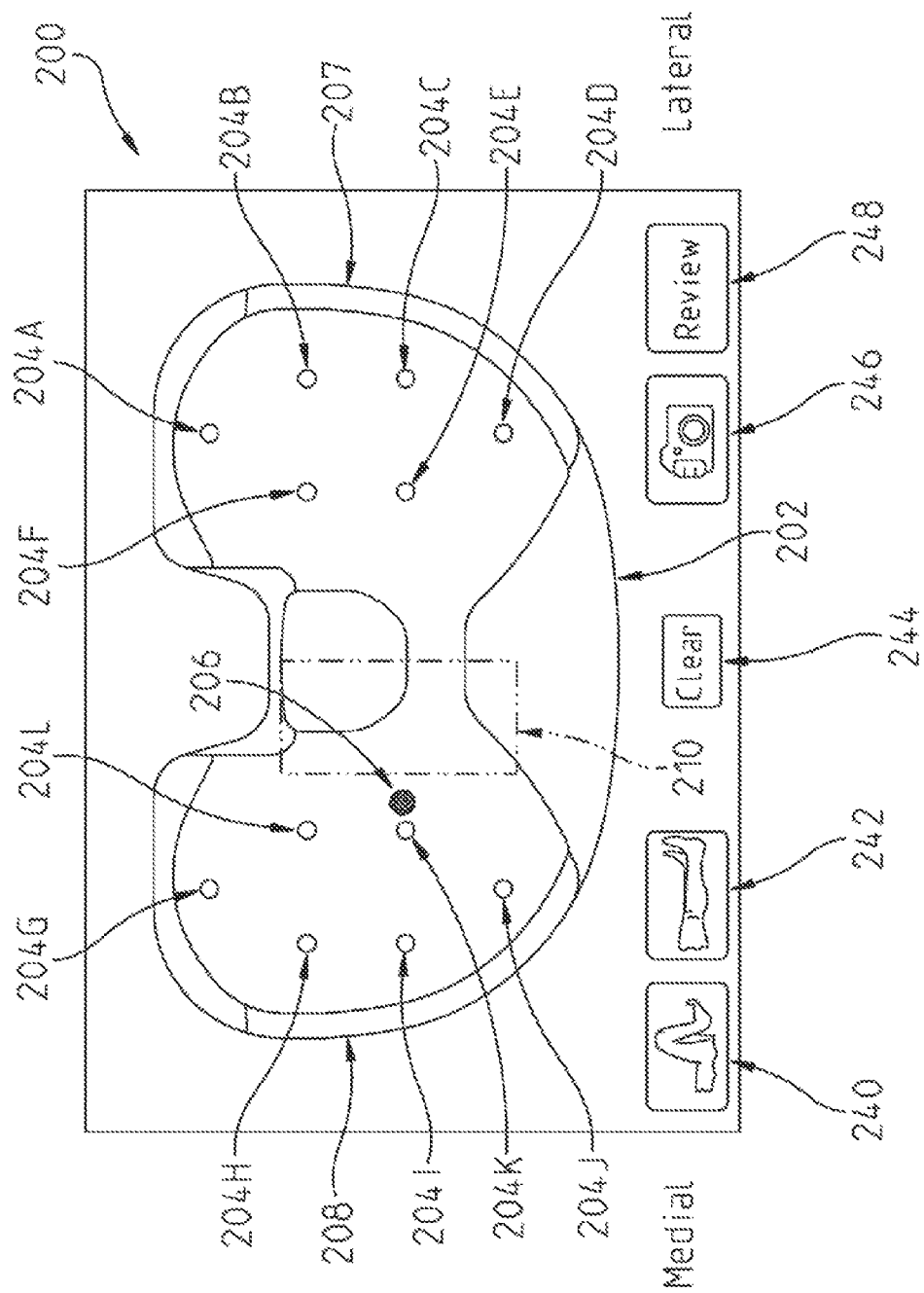
FIG. 7 is a representative view of the exemplary display screen of FIG. 5 of the user interface of the exemplary computing system of FIG. 3 wherein the force center indicator is medialized.
Figure 8:
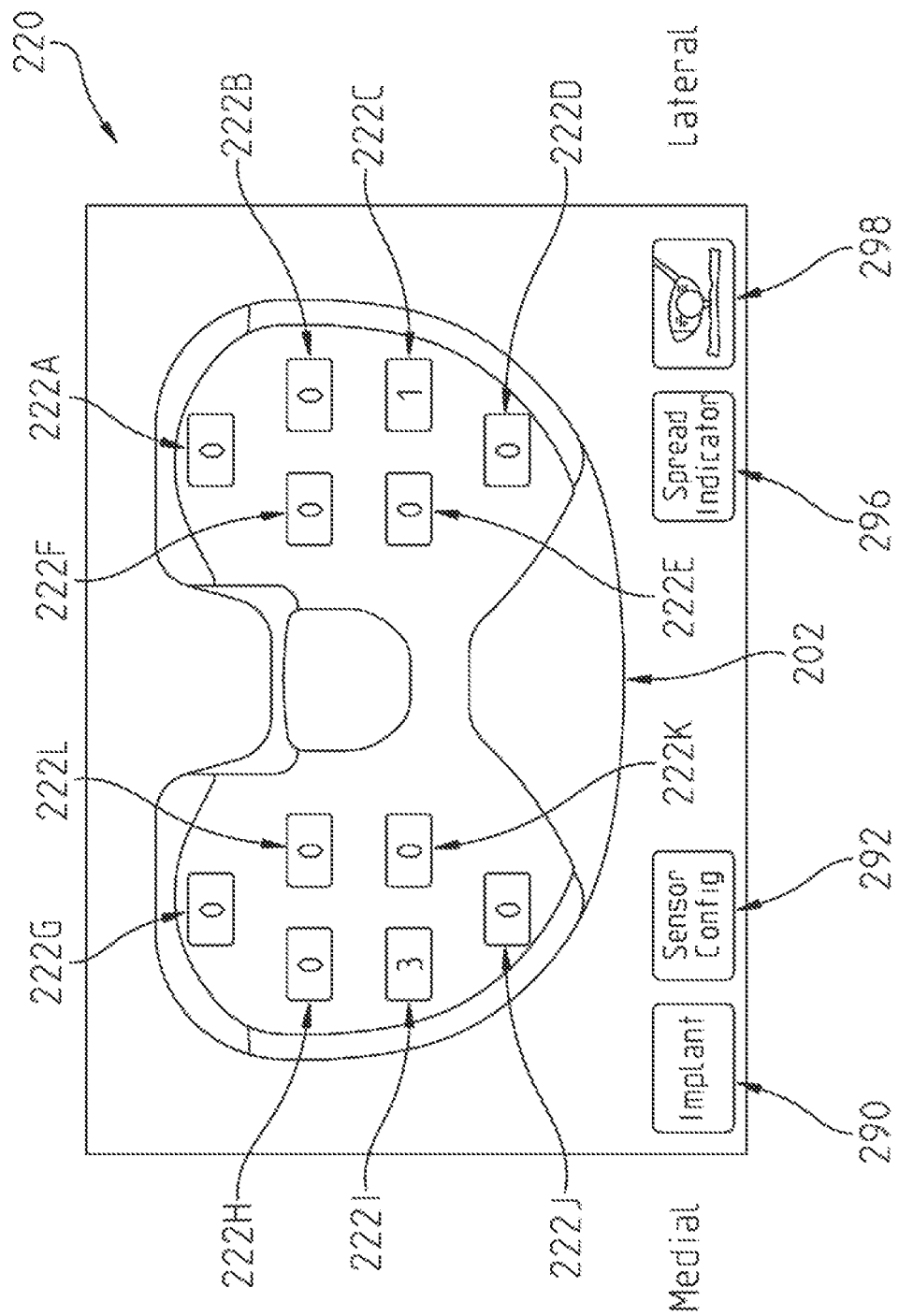
FIG. 8 is a representative view of the exemplary display screen of FIG. 6 corresponding to the force magnitude experienced by the sensors of the sensing provisional of FIG. 1 for FIG. 7.
Figure 9:
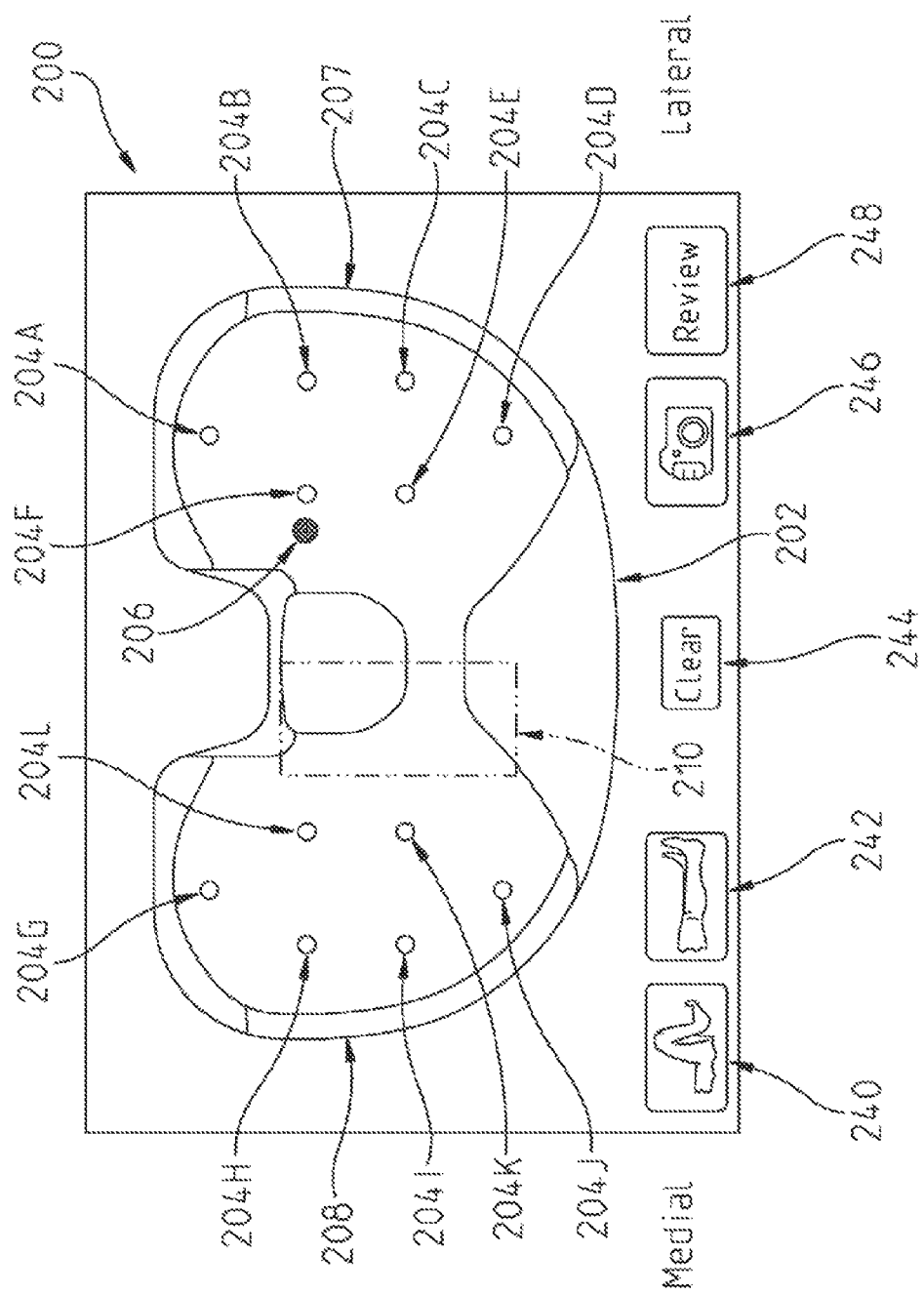
FIG. 9 is a representative view of the exemplary display screen of FIG. 5 of the user interface of the exemplary computing system of FIG. 3 wherein the force center indicator is lateralized.
Figure 10:
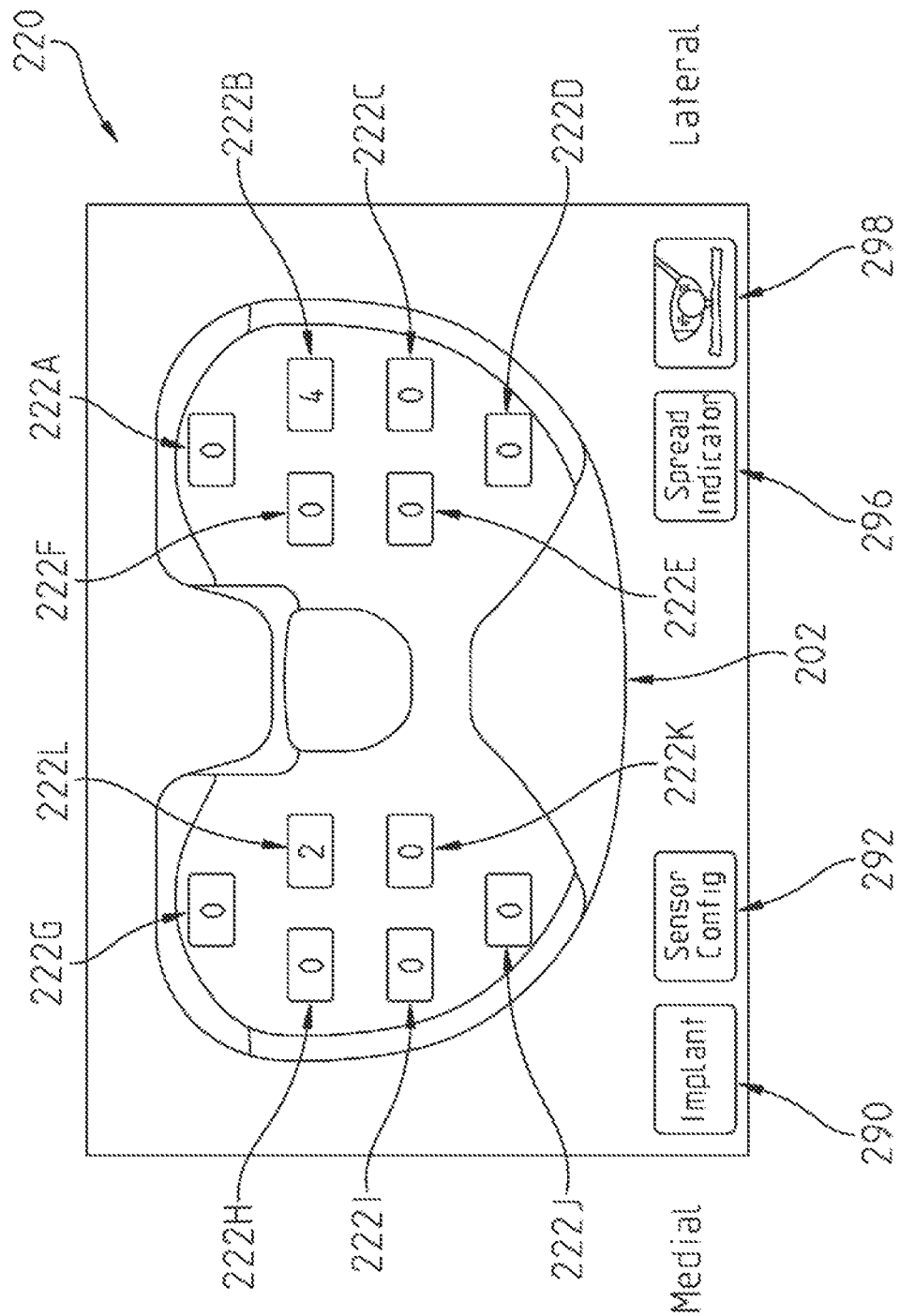
FIG. 10 is a representative view of the exemplary display screen of FIG. 6 corresponding to the force magnitude experienced by the sensors of the sensing provisional of FIG. 1 for FIG. 9.
Figure 11:
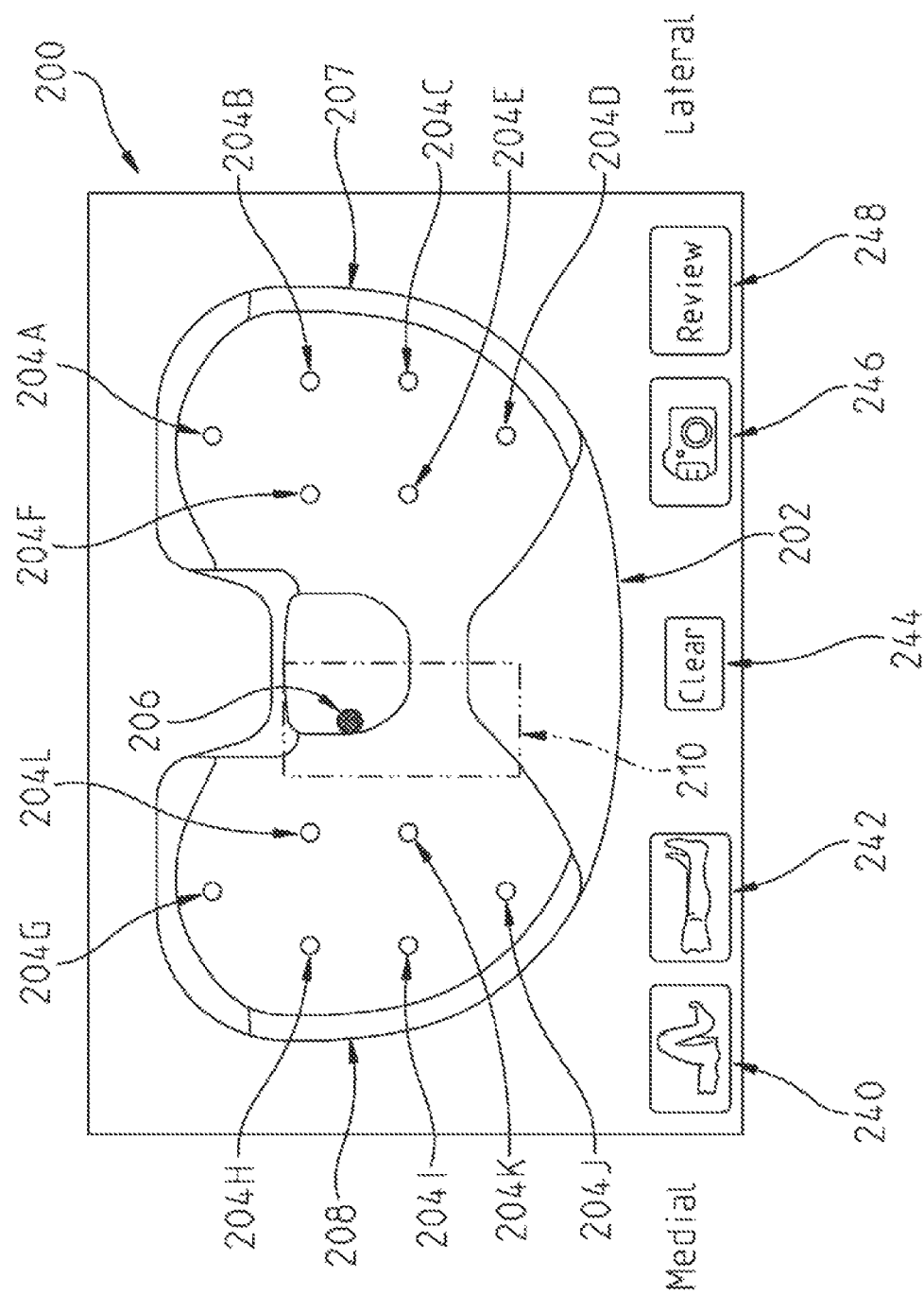
FIG. 11 is a representative view of the exemplary display screen of FIG. 5 of the user interface of the exemplary computing system of FIG. 3 wherein the force center indicator is positioned at a desired location for the force center.
Figure 12:
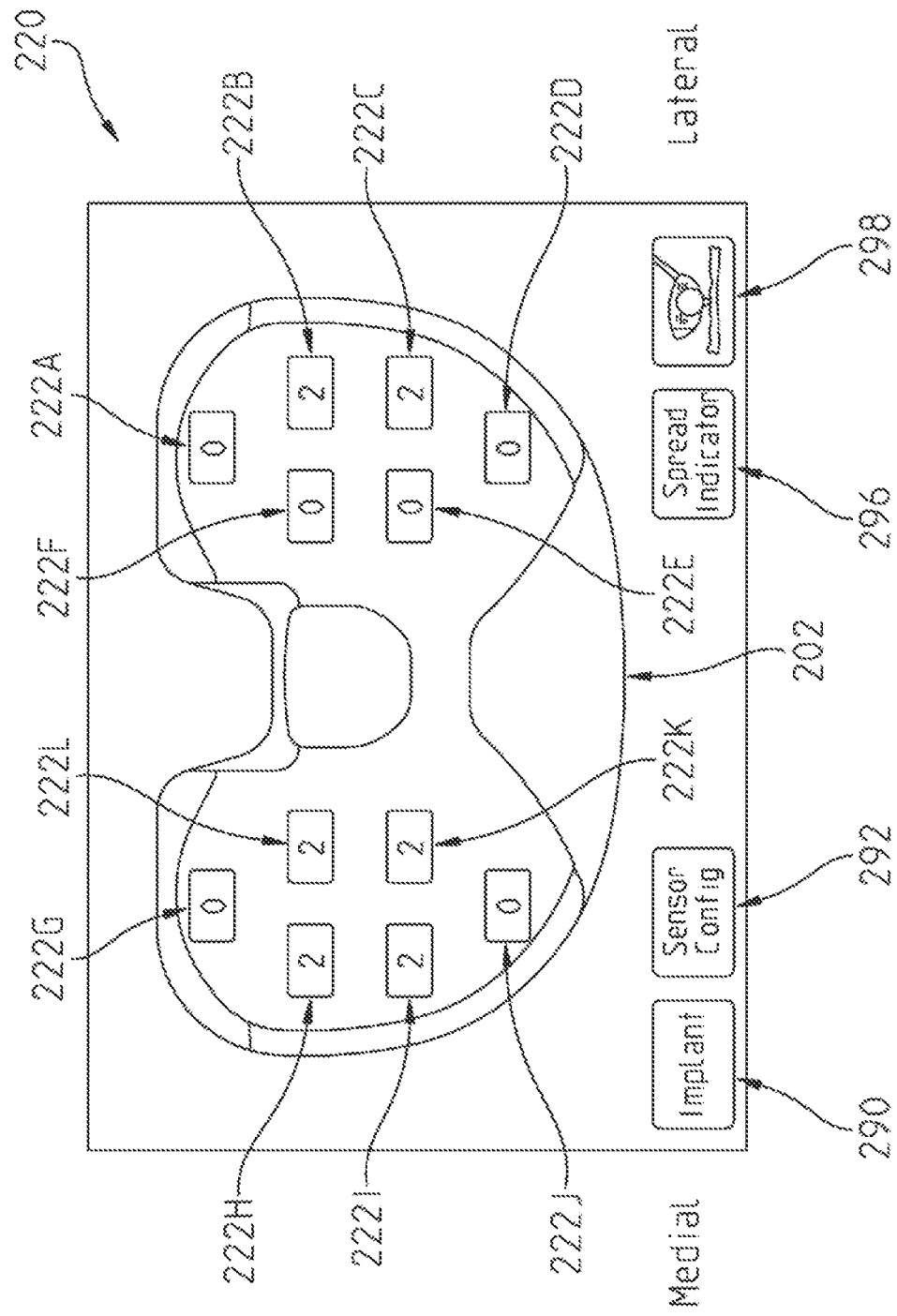
FIG. 12 is a representative view of the exemplary display screen of FIG. 6 corresponding to the force magnitude experienced by the sensors of the sensing provisional of FIG. 1 for FIG. 11.

As shown in FIG. 6, the value corresponding to each of sensor icons 222 is a "0" value. Since all of the sensors 42 has a "0" value, mean force center indicator 206 is shown in the exact center of provisional representation 202. Referring to FIGS. 7 and 8, display screen 200 and display screen 220 illustrate the location of mean force center indicator 206 when the force distribution of force sensors 204 is far medialized. Referring to FIGS. 9 and 10, display screen 200 and display screen 220 illustrate the location of mean force center indicator 206 when the force distribution of force sensors 204 is far lateralized. Referring to FIGS. 11 and 12, display screen 200 and display screen 220 illustrate the location of mean force center indicator 206 when the force distribution of force sensors 204 results in mean force center indicator 206 being located within the perimeter of bounded area 210.

In one embodiment, display screen 200 and display screen 220 are displayed at the same time on a display 132. In one embodiment, display screen 200 and display screen 220 are not displayed simultaneously on a display 132. In this embodiment, an input is provided to toggle between display screen 200 and display screen 220.

Figure 13:
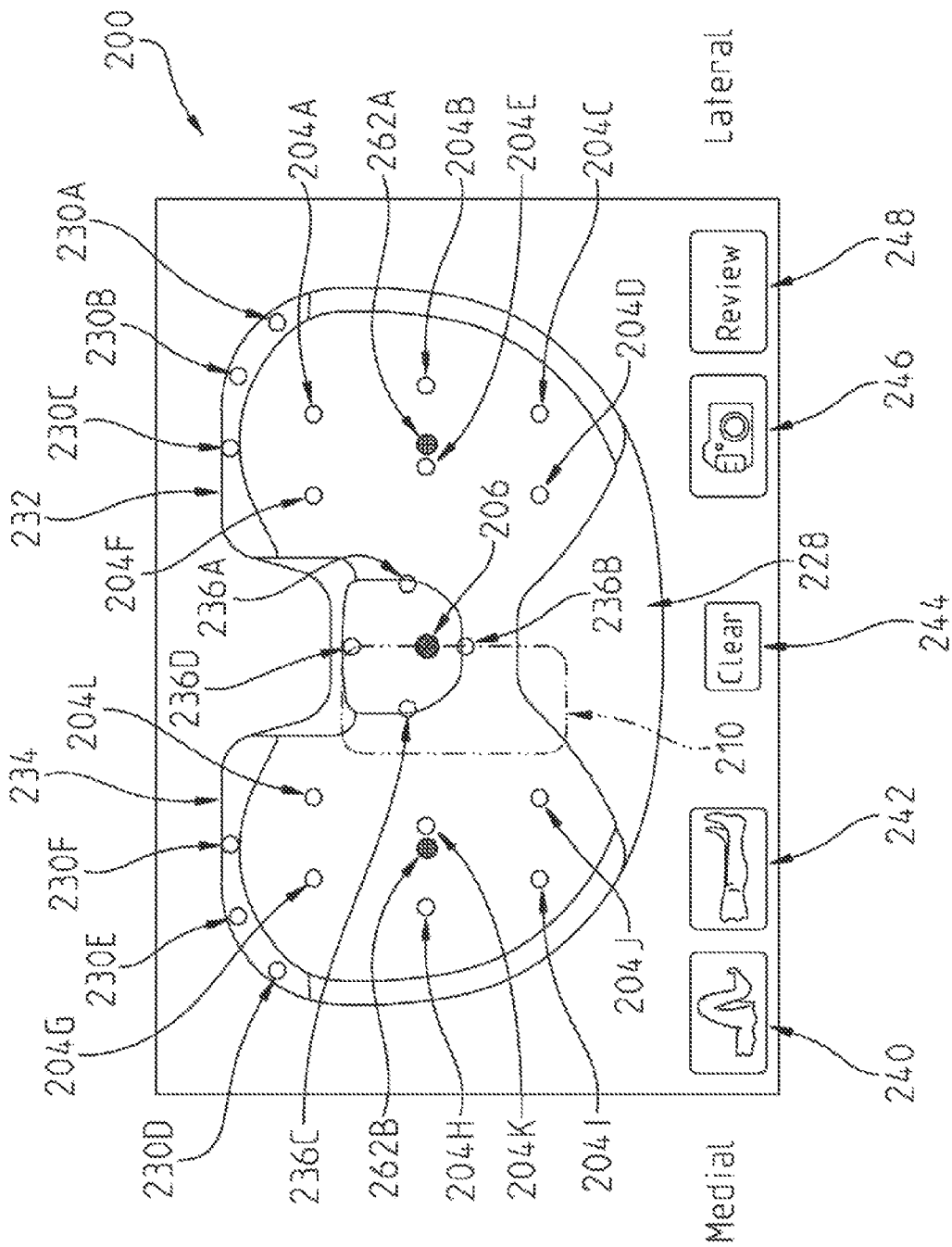
FIG. 13 is a representative view of the exemplary display screen of FIG. 5 of the user interface of the exemplary computing system of FIG. 3 related to another exemplary sensing provisional which includes sensors along the posterior ridge of the provisional and sensors related to a post region of the provisional.

Referring to FIG. 13, display screen 200 illustrates an image of another exemplary tibia provisional 228. Tibia provisional 228 includes twelve force sensors, represented by sensor icons 204A-L. The sensors are divided into two groups. A first group including sensors 204A-F and a second group including sensors 204G-L. In addition, tibia provisional 228 includes a plurality of sensors, represented by sensor icons 230A-C, which are positioned along the lateral posterior ridge 232 of tibia provisional 228 and a plurality of sensors, represented by sensor icons 230D-F, which are positioned along the medial posterior ridge 234 of tibia provisional 228. Exemplary force sensors for positioning along the posterior ridge include force sensing resistor or capacitive flex circuits, piezoelectric film, piezoelectric elements, piezoresistive and piezoelectric polymers, metal foil strain gages, semiconductor strain gages, piezoresistive and capacitive pressure sensors, interferometric optical sensors, path displacement optical sensors, optical fiber force sensors, and other suitable sensing technologies. Sensors 230A-F monitor force placed on the respective posterior ridge of tibia provisional 228 due to the femur 16 rolling upon or otherwise impacting the posterior ridge of tibia provisional 228.

Tibia provisional 228 also includes a plurality of sensors, represented by sensor icons 236A-D, which are positioned proximate the post of tibia provisional 228. The post of tibia provisional 228 is positioned under a central, posterior portion of the contoured top surface 24 of tibia provisional 228. The post is received in a recess in resection surface 14 of tibia 12. In one embodiment, sensors 236 are strain gages located under the spine of tibia provisional 228. The strain data is communicated to computing system 100 and is represented on display screen 200 to provide an indication to the operator of the amount of strain experienced by the post region of tibia provisional 228. The operator may use this information to determine if the amount of force being applied on the spine of tibia provisional 228 requires surgical action or an upgrade to another implant type.

As shown in FIG. 13, mean force center indicator 206 is still represented. Further, a compartment force center indicator 262 is provided for each group of sensors. In the illustrated embodiment, force center 262A is provided for sensors 204A-F and force center 262B is provided for sensors 204G-L. In the illustrated embodiment, circular dots represent the force centers 262A-B and mean force center indicator 206. In one embodiment, force center 262A-B are shown in a first color and mean force center indicator 206 is shown in a second color. In one embodiment, force center 262A-B and mean force center indicator 206 are illustrated in other ways to distinguish between force center 262A-B and mean force center indicator 206.

In one embodiment, the location of each of force center 262A-B is determined by summing the vectors to each sensor from the centroid position of the sensors times the force above a bias or noise level experienced by the respective sensor. The summed value is divided by the sum of the forces from all of the sensors 204 within the respective group. The respective force center location is an offset from the centroid location by the vector provided by the above calculation.

The mean force center indicator 206 may be determined in the same manner by considering all of the sensors 204A-L. In one embodiment, wherein there are two groups of sensors 204, mean force center indicator 206 is located at a midpoint of a line connecting the compartment force center indicator 262 of each of the two groups of sensors.

Figure 13A:
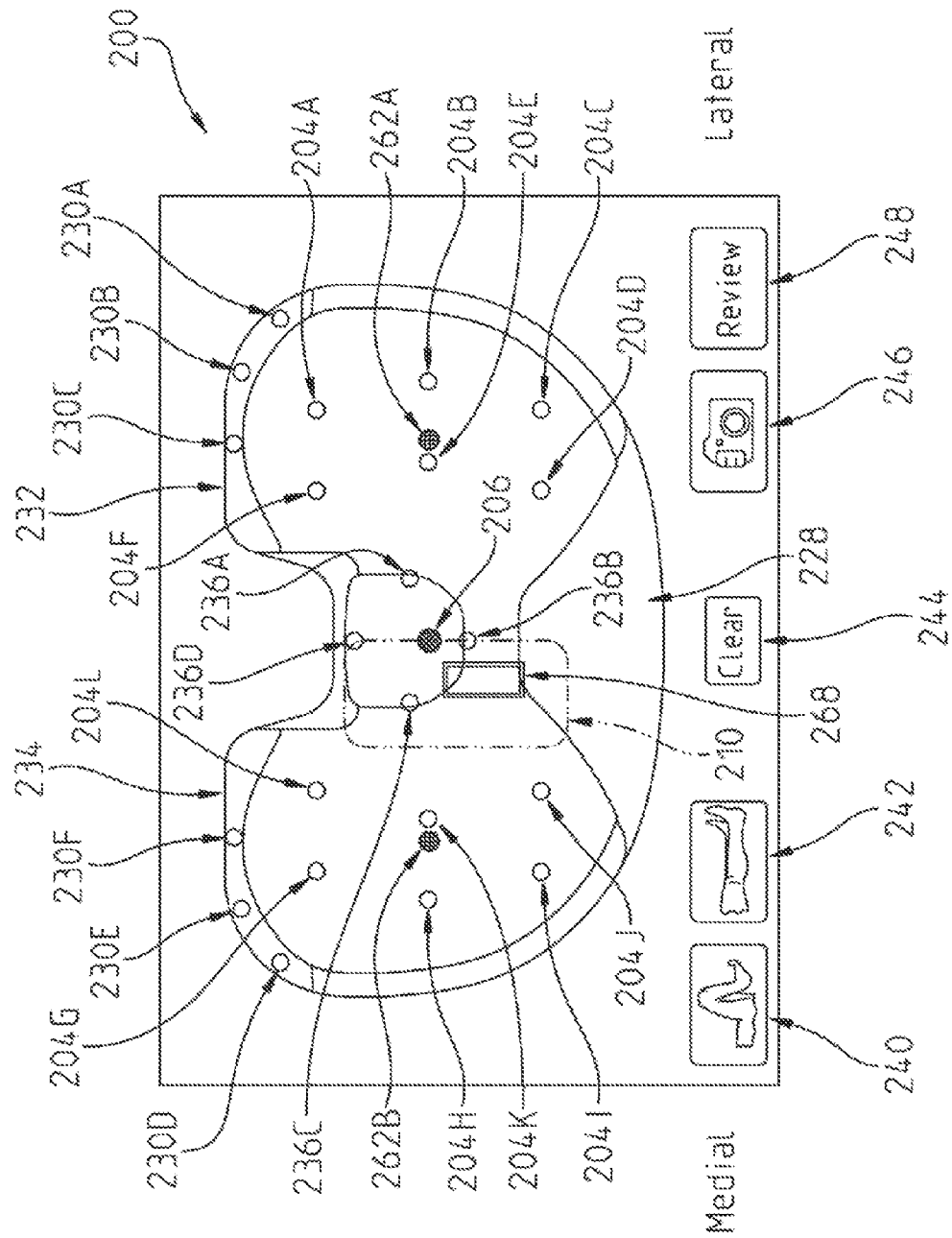
FIG. 13A is a representative view of the exemplary display screen of FIG. 13 including a representation of a multi-level representation of a desired location for the force center and force centers for each sensor compartment of the sensing provisional.

Referring to FIG. 13A, another exemplary display screen 200 is shown wherein bounded area 210 includes multiple levels. A first level, bounded by the perimeter of bounded area 210, represents the area corresponding to a structurally sound knee. A second level, bounded by a region 268, is a sub-region of bounded area 210 and represents an area corresponding to an optimized knee.

In one embodiment, a user may change the shape and/or size of one or both of bounded area 210 and region 268. Exemplary methods of adjusting the characteristics of bounded area 210 and region 268 include selection from a number of predefined shapes in a preferences menu or via a touch/drag technique through display screen 200. Exemplary touch/drag techniques include a multi-touch method for increasing the width or height of either indicator.

Figure 14:
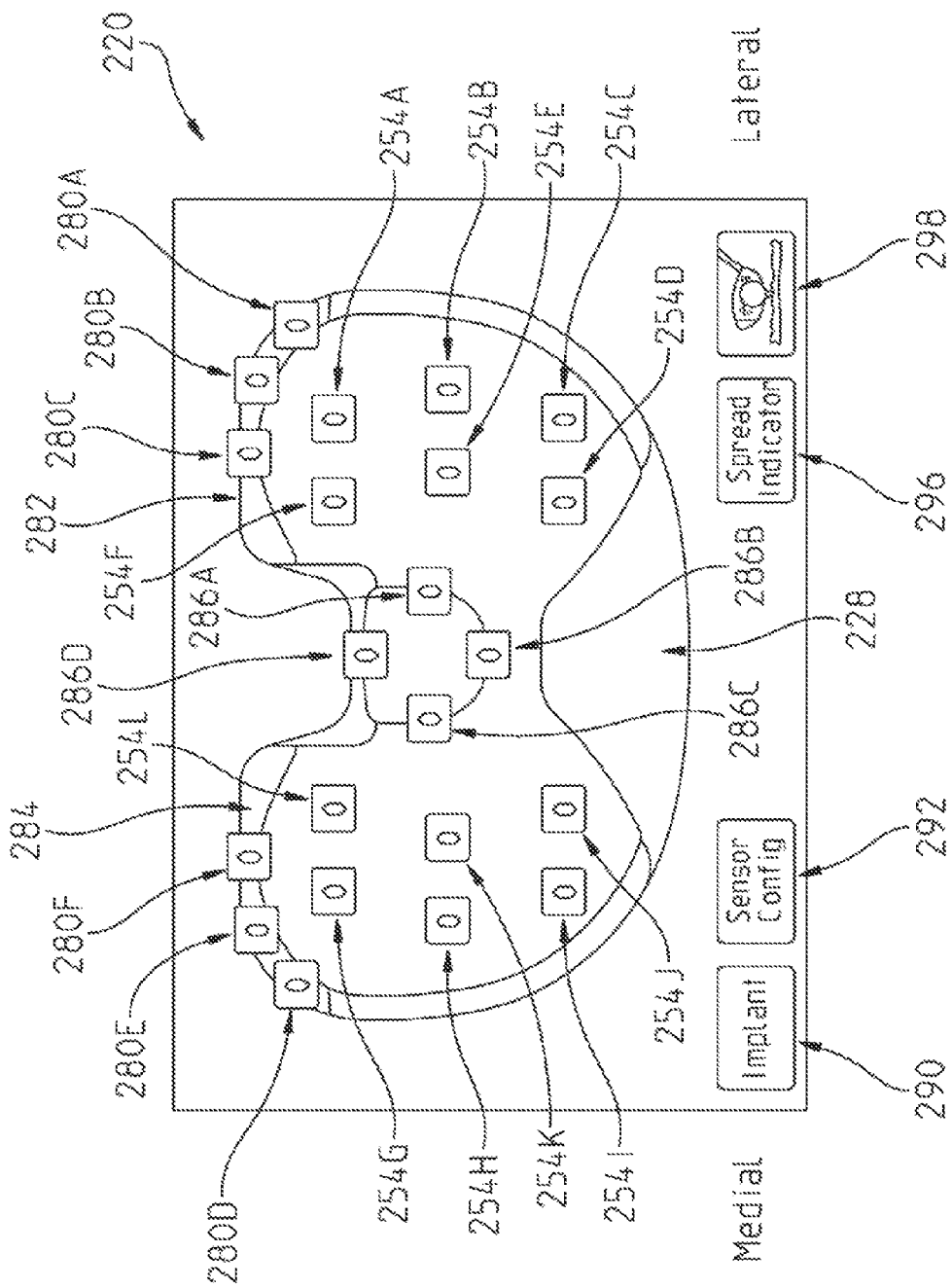
FIG. 14 is a representative view of the exemplary display screen of FIG. 6 corresponding to the force magnitude experienced by the sensors of the sensing provisional of FIG. 13.

Referring to FIG. 14, display screen 220 displays sensor icons 254A-L for sensors 204A-L, sensor icons 280A-F for sensors 230A-F, and sensor icons 286A-D for sensors 236A-D. The sensor icons function in the same manner as sensor icons 222. In one embodiment, display screen 200 and display screen 220 are displayed simultaneously on a display device 132 associated with computing system 100.

Figure 15:
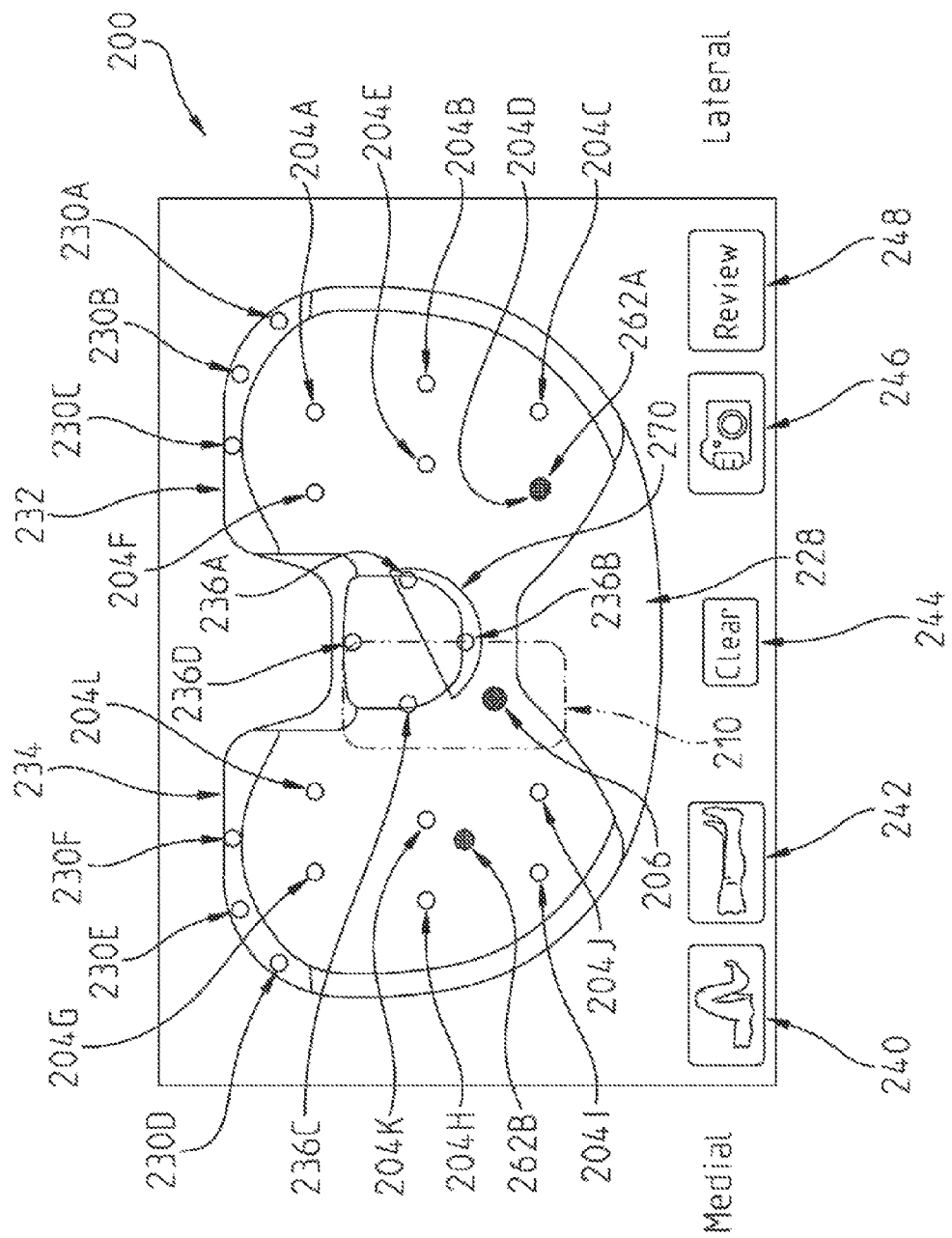
FIG. 15 is a representative view of the exemplary display screen of FIG. 13 including a representation of a force indicator related to the post region of the provisional.
Figure 16:
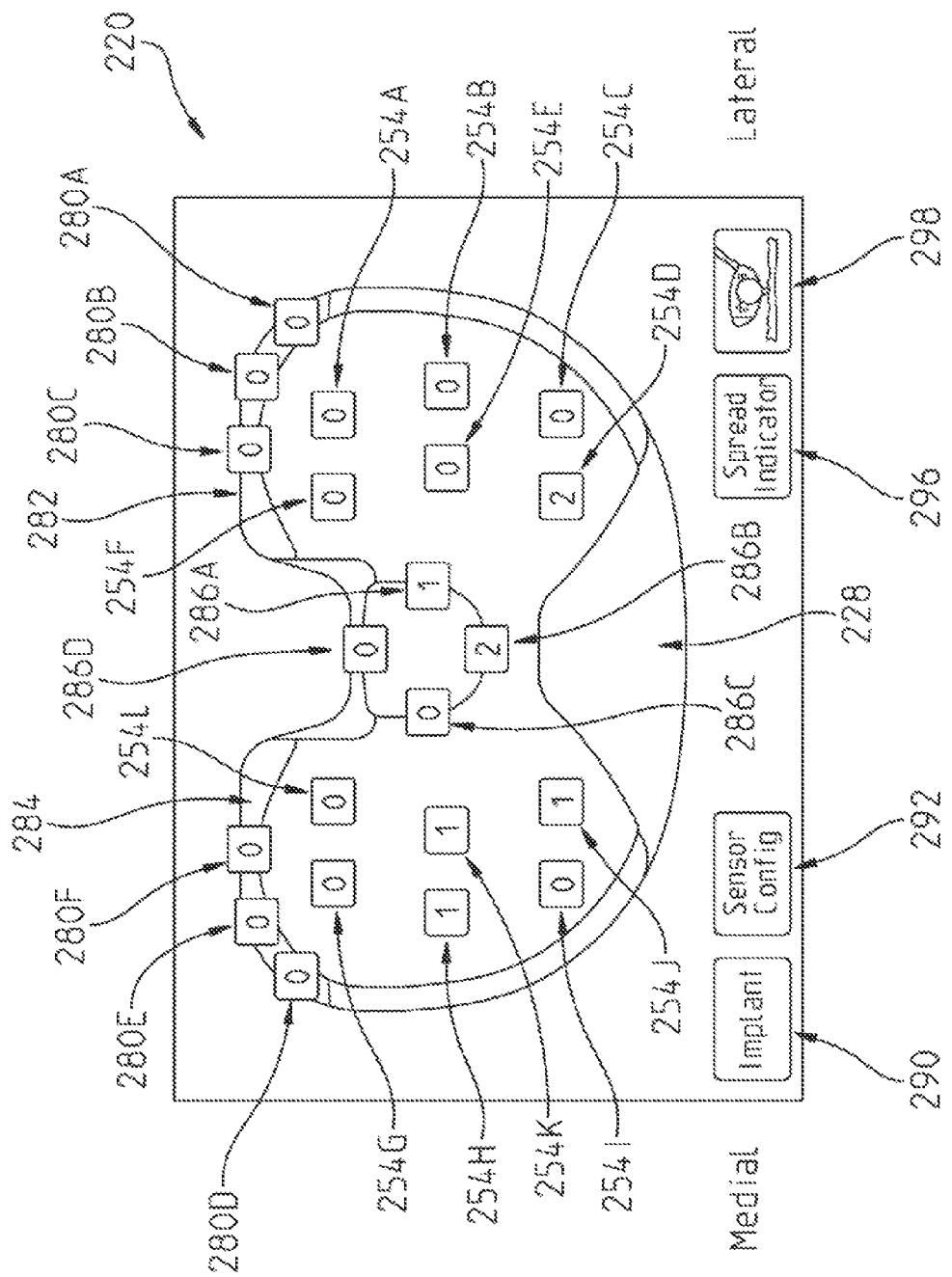
FIG. 16 is a representative view of the exemplary display screen of FIG. 6 corresponding to the force magnitude experienced by the sensors of the sensing provisional of FIG. 15.

Referring to FIG. 16, the sensor values for sensor 204D (represented by sensor 254D), sensor 204H (represented by sensor 254H), sensor 204J (represented by sensor 254J), sensor 204K (represented by sensor 254K), sensor 236A (represented by sensor icon 286A), and sensor 236A (represented by sensor icon 286A) have changed from FIG. 14. The result of this change is illustrated in FIG. 15. As shown in FIG. 15, the location of force center 262A (which now coincides generally with the location of sensor 204D), force center 262B, and mean force center indicator 206 have changed.

In addition to mean force center indicator 206 and 262A-B, display screen 200 in FIG. 15 includes a representation 270 of the forces experienced by the post region of tibia provisional 228. Representation 270 provides both an indication of the magnitude of the force in the post region of tibia provisional 228 and the portions of the post region experiencing the greater force. In the illustrated embodiment, representation 270 is circular and as the force magnitude increases the shape of representation 270 sweeps through a larger arc. At smaller force magnitudes, the shape of representation 270 is generally semi-circular while at larger forces the shape of representation 270 is generally about 300 degrees of a circle. In one embodiment, as the force magnitude increases a color and/or intensity of representation 270 changes. As an example, when the force exceeds a threshold a color of the representation changes to red indicating that there is excessive force on the post. The arc portion of representation 270 is centered on the perimeter portion of the post experiencing the most force. The magnitude and force direction of the post area, in one embodiment, is determined by the values of sensors 236A-D. In one example, the magnitude is a sum of the force recorded by sensors 236A-D and the direction is provided by having the midpoint of the arc portion located at the location of the one of sensors 236A-D having the largest force reading or if two sensors 236A-D have the same force reading then the midpoint of the arc portion is located halfway between the location of the two sensors 236A-D. The magnitude and force direction of the post area, in one embodiment, is determined by the values of sensors 236A-D and at least one of sensors 204A-L and sensors 230A-F.

Figure 17:
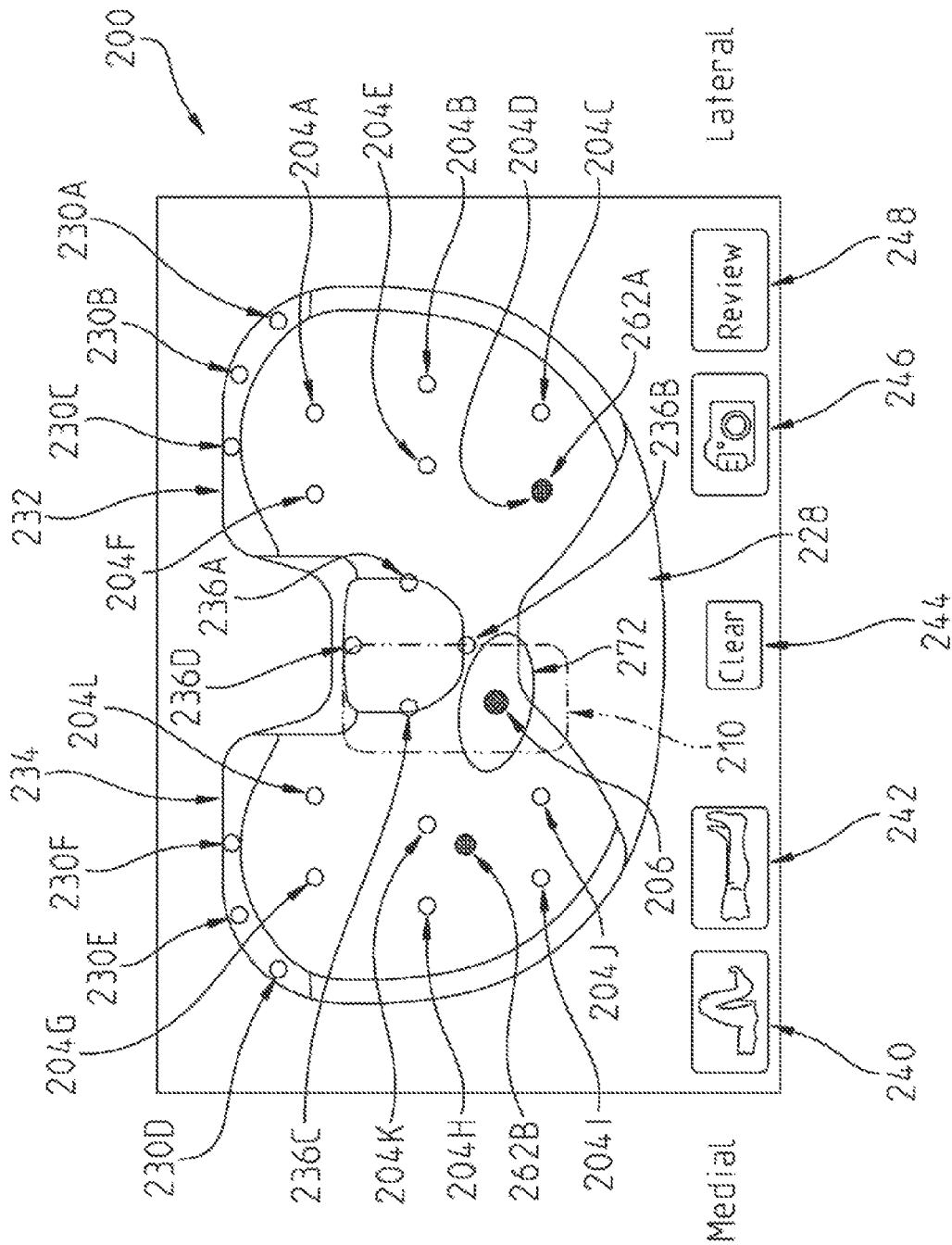
FIG. 17 is a representative view of the exemplary display screen of FIG. 13 including a representation of an exemplary spread force indicator.

Referring to FIG. 17, an exemplary spread indicator 272 is shown. The sensor force values in FIG. 17 are the same as FIG. 16. Spread indicator is a visual representation, such as an oval or other geometric shape, displayed around mean force center indicator 206 to indicate the spread of the forces across the surface of tibia provisional 228. In one embodiment, the spread indicator 272 is an oval shape and the ratio of the major and minor axis lengths provides an indication of the distance between force center 262A and force center 262B. A flatter oval correlates to a greater distance between force center 262A and force center 262B.

In one embodiment, spread indicator 272 provides an indication of the relationship of condylar forces. In one example, an overall size of spread indicator 272 indicates a magnitude of the forces been applied to the tibial surface of tibia provisional 228. The less force the smaller the oval, the greater the force the bigger the oval.

In one embodiment, spread indicator 272 is an oval and a linear regression is performed determine the best fit line to a collection of points; where the points are placed along the vector from the sensor centroid position to each sensor, weighted in distance by both the actual distance to the sensor from the centroid and the force reading of the sensor. The resulting best fit line would define the major axis of the oval indicator 272. A measure of the line fit error across the points, such as the RMS error, would define the width of the oval indicator 272 relative to its length. For example, if all points fit well to the line, the oval indicator 272 would be flat, whereas if there is no correspondence to a line for the point spread, the oval indicator 272 would be circular.

Figure 18:
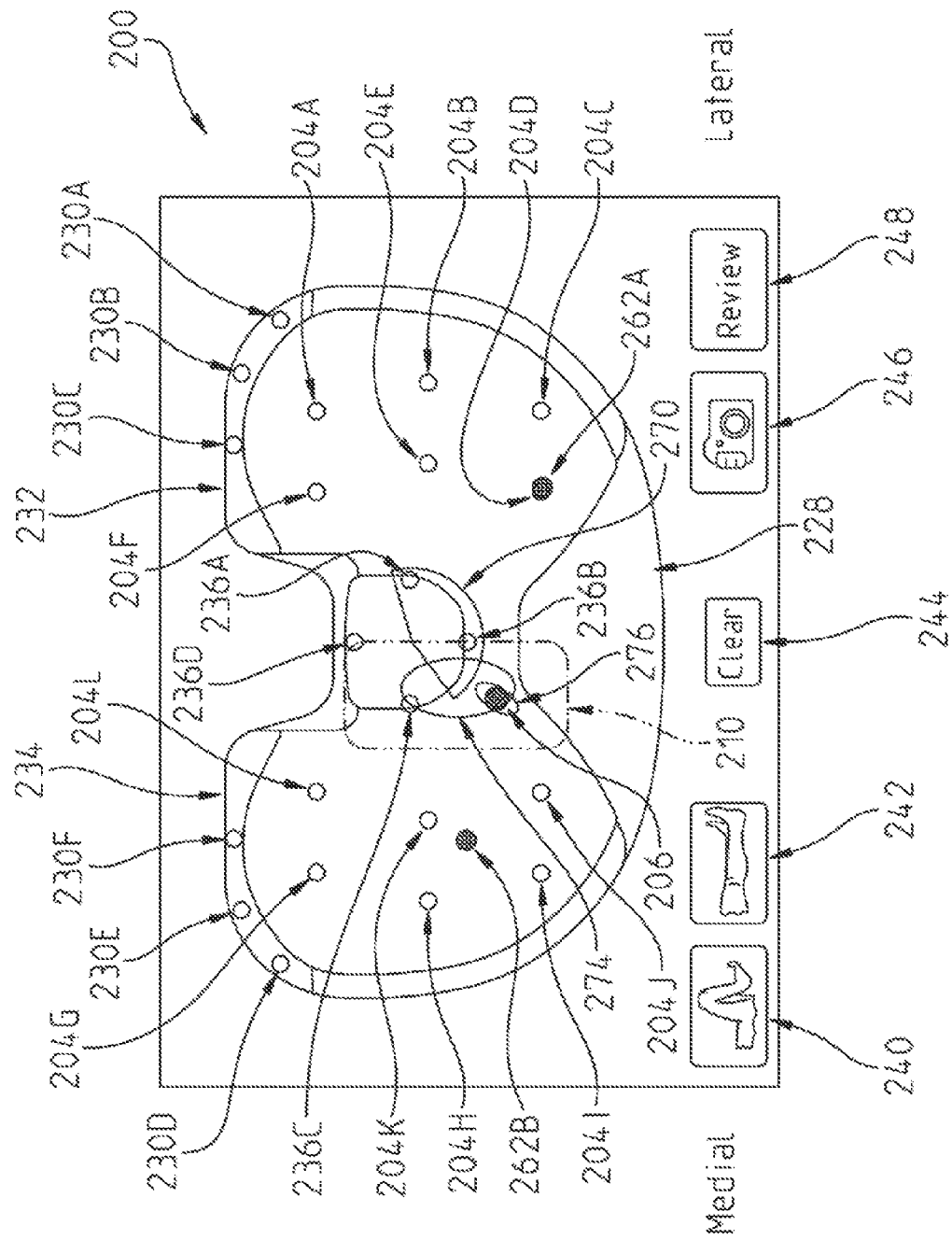
FIG. 18 is a representative view of the exemplary display screen of FIG. 13 including a representation of another exemplary spread force indicator and a force indicator related to the post region of the provisional.

Referring to FIG. 18, an exemplary spread indicator 274 is shown. The sensor force values in FIG. 18 are the same as FIG. 16. Spread indicator 274 is a visual representation, such as an oval or other geometric shape, displayed around mean force center indicator 206 to indicate the spread of the forces across the surface of tibia provisional 228.

In the illustrated embodiment, the spread indicator 274 is an oval shape and the average position of compartment force center indicator 262 relative to its compartment center for both of the compartment force indicators 262A-B could be used to position the oval about the overall force indicator such that the oval center is offset from the overall force center in a way that indicates where the average compartment force is relative to the compartment force centers. For example, if both of the compartment force indicators are at the medial extremes of their compartments, the oval would appear about the overall force center dot such that the dot would be located at the medial side of the oval. A second spread indicator 276 provides an indication of the spread of the compartment force centers away from the average location of each within their respective compartment. The spread would be used to stretch the oval in the direction of the spread. For example, if the medial condyle indicator 262B was at an extreme medial position within its compartment and the lateral condyle indicator 262A was at a lateral position within its compartment, the oval would appear to be 'fat', and if the medial indicator 262B was lateral, with the lateral indicator 262A was medial, the oval would be 'skinny'. If both force indicators 262A and 262B were located medially, the oval would be circular.

In another such instance of a spread indicator, circles would appear about each of the compartment force indicators 262A-B in addition to, or instead of, the mean force center indicator 206. In this case, the size of the circles about force indicators 262A-B would indicate the magnitude of the overall compartment force and/or the overall force, possibly in addition to the positional shift of spread indicator 274 described above.

Figure 19:
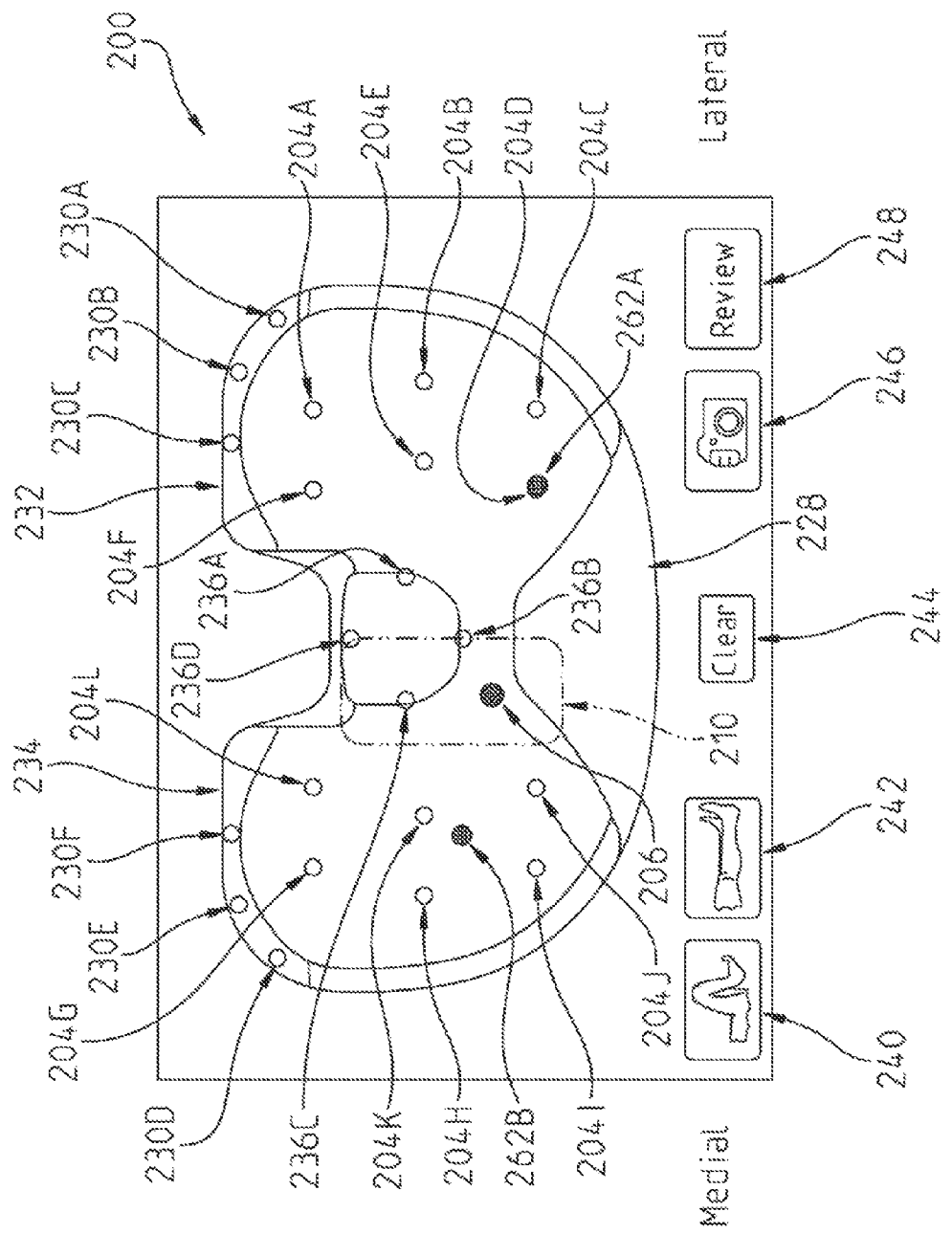
FIG. 19 is a representative view of the exemplary display screen of FIG. 13 wherein the current locations of the force indicators are marked as corresponding to a full flexion position of the knee joint.

Referring to FIG. 19, the forces acting on the sensors 236A-D have been removed. Assuming the knee joint 10 is in full flexion at this point, the operator may note this configuration of knee joint 10 by selecting input button 240, which in one embodiment, is a soft key on a touch screen. Computing system 100 stores the location values of force center 262A and force center 262B in force database 116. The operator may now move the knee joint 10 to a fully extended position to observe the forces in the new position. These forces are illustrated in FIG. 20

Figure 20:
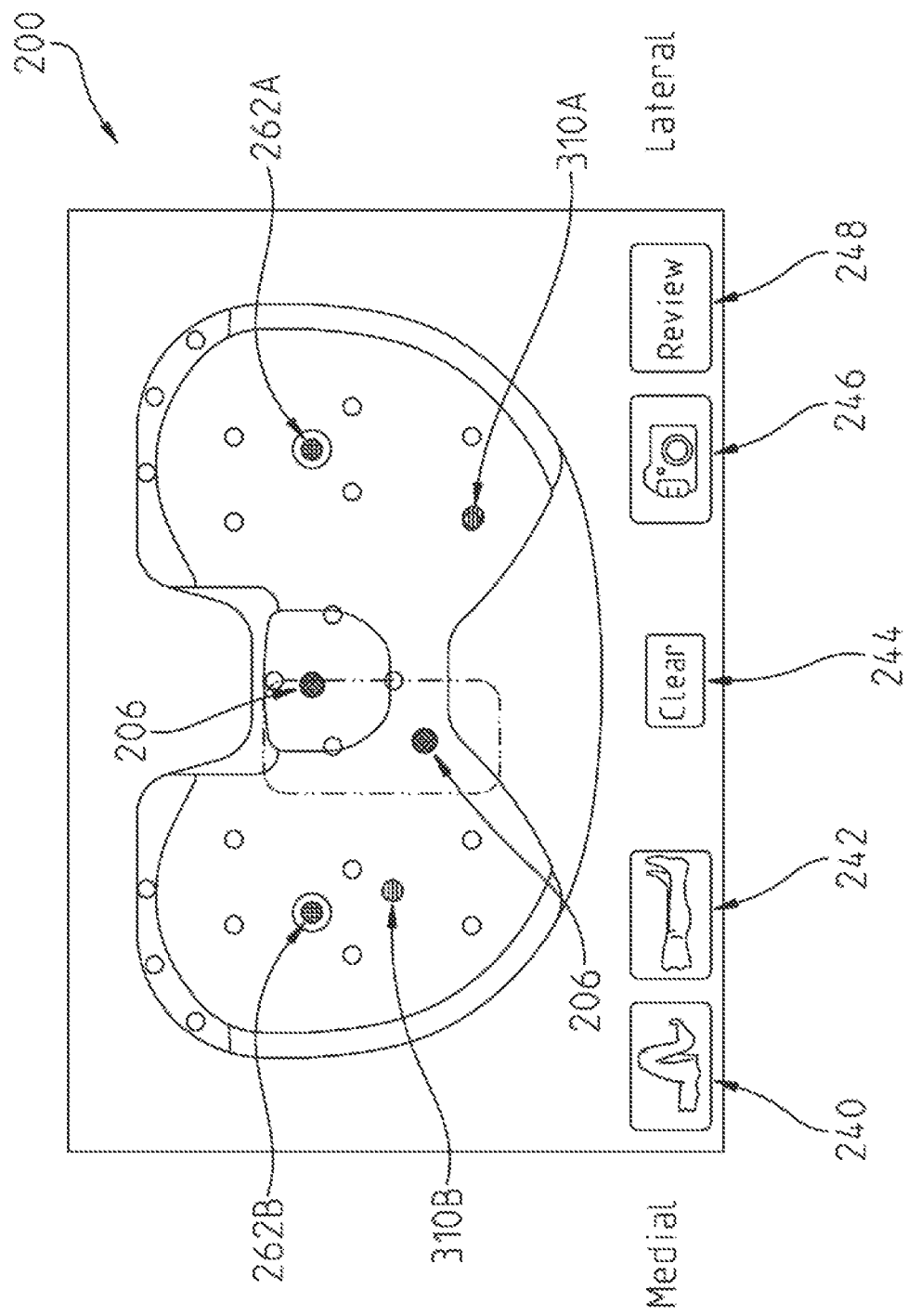
FIG. 20 is a representative view of the exemplary display screen of FIG. 13 wherein the current locations of the force indicators are marked as corresponding to a full extension position of the knee joint and including historical markers associated with the current locations of the force indicators are marked as corresponding to the full flexion position of the knee joint in FIG. 19.
Figure 21:
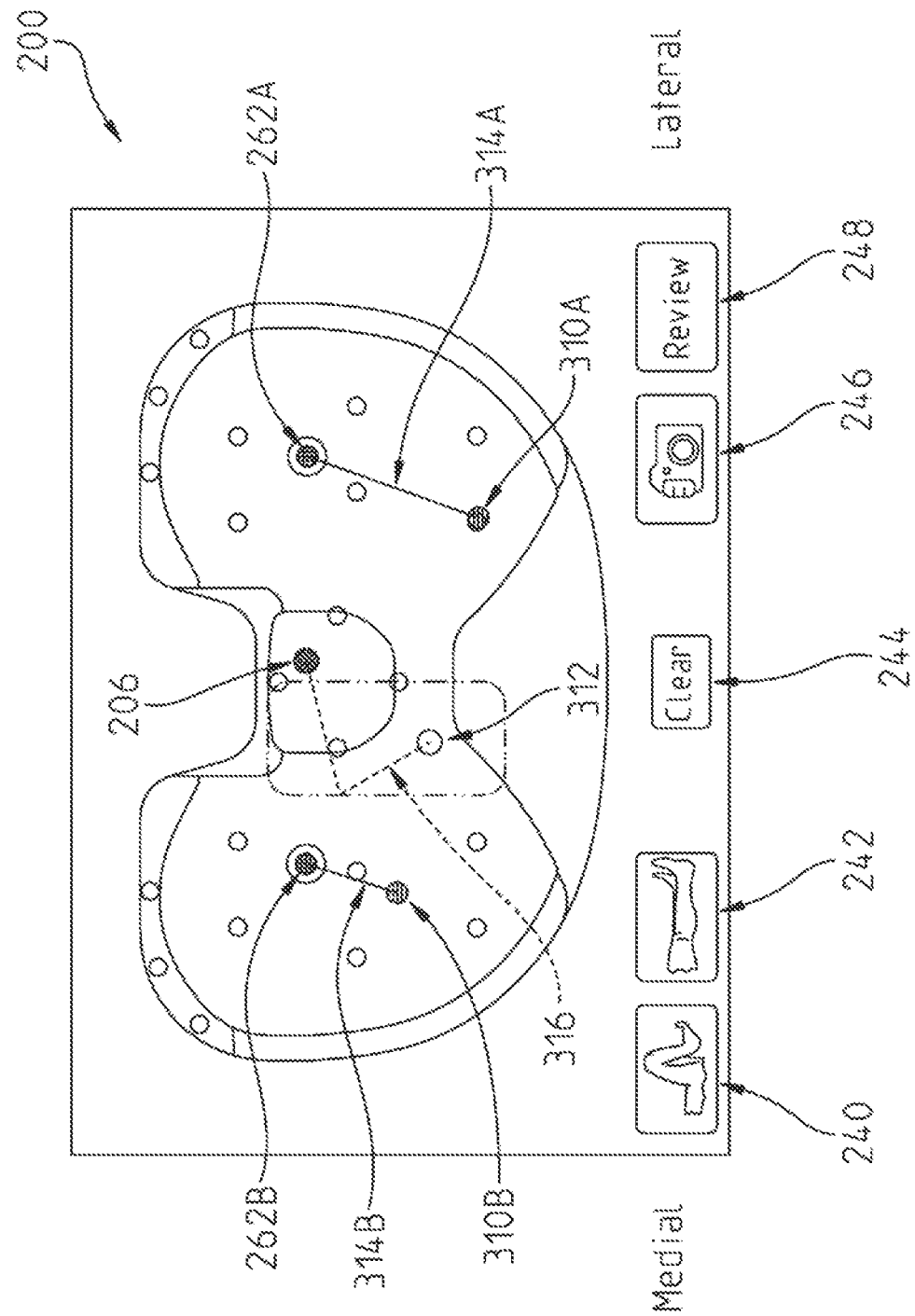
FIG. 21 is a representative view of the exemplary display screen of FIG. 13 wherein the current locations of the force indicators are marked as corresponding to a full extension position of the knee joint and including historical markers associated with the current locations of the force indicators are marked as corresponding to the full flexion position of the knee joint in FIG. 19 and path indicators which provide the relative positions of the force indicators as the knee was at positions between full flexion and full extension.

Referring to FIG. 20, force center 262A and force center 262B have moved due to changes in force experienced by tibia provisional 228. The locations marked in the full flexion position of knee joint 10 remain shown on display screen 200 for reference by the operator as icons 310A-B. In one embodiment, the color of icons 310A-B corresponds to a color of select input button 242. Now that the knee joint 10 is in full extension, an operator may select input button 242 to indicate that the knee is in full extension. Computing system 100 will store these extension positions of force center 262A-B in force database 116. In a similar fashion, for both flexion and extension, computing system 100 stores the location values of mean force center indicator 206 in the force database 116.

In one embodiment, computing system 100 in addition to mean force center indicator 206, force center 262A-B, and the historical markers 310A-B and 312, also illustrates the path that each of mean force center indicator 206 and force centers 262A-B take from the respective historical markers positions 310A-B and 312 to their current positions. These paths are illustrated as paths 314A-B and 316, respectively. In one embodiment, a size of the path elements, illustratively dots, spacing of path elements, or color intensity of path elements may be varied to indicate the speed of change of the force during the motion. In one embodiment, each path may fade or be selectively erased in a variety of ways, including but not limited to time based techniques, having a maximum trail length, and resetting the trail when the flexion button 240, extension button 242, or clear button 244 is selected. The clear button erases all historical markers from display screen 200.

Figure 22:
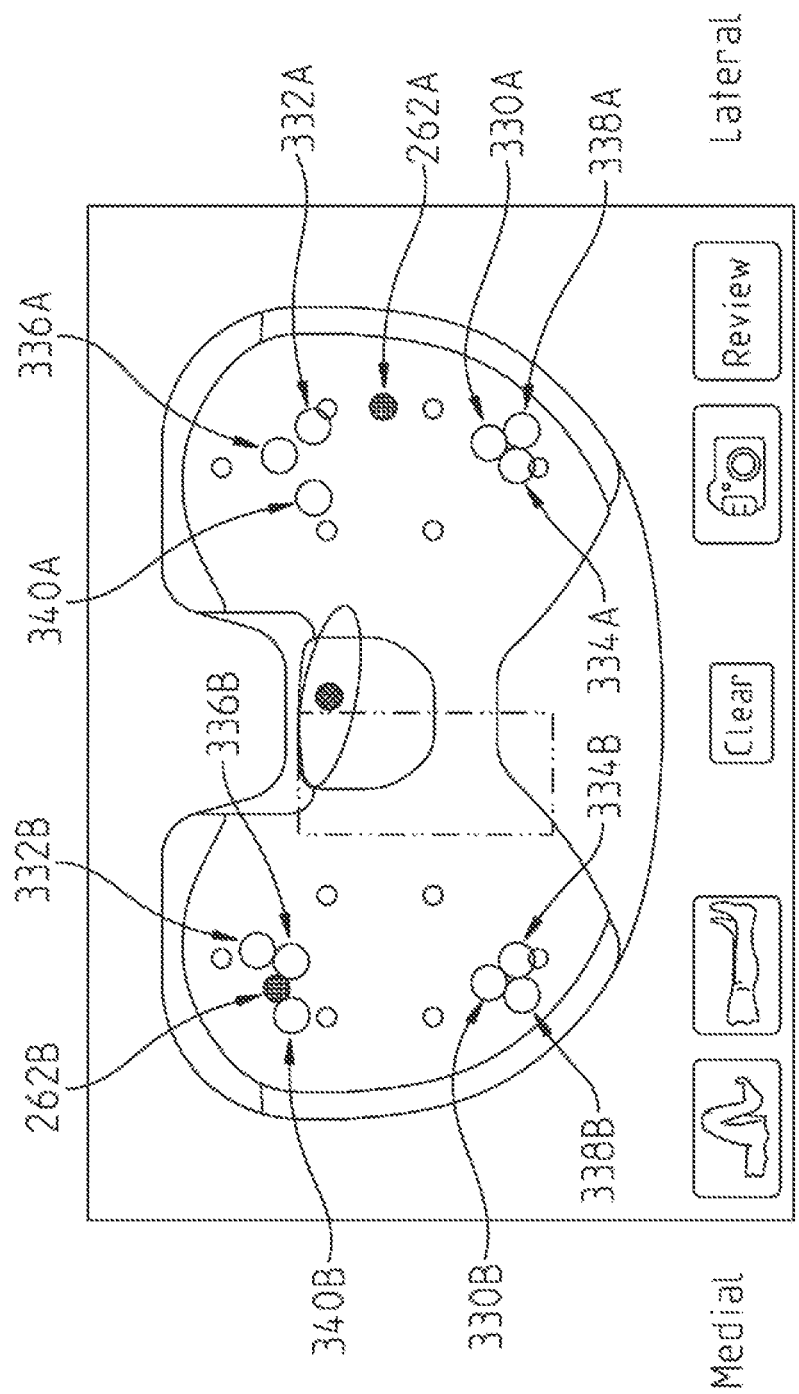
FIG. 22 is a representative view of the exemplary display screen of FIG. 13 wherein the current locations of the force indicators are marked and including historical markers associated with multiple trials of the knee joint at full flexion and full extension.

In one embodiment, computing system 100 retains multiple instances of the historical markers for both flexion and extension in database 116. Referring to FIG. 22, markers 330A-B correspond to the compartment force centers for a first reading of the knee joint 10 in one of flexion and extension and markers 332A-B correspond to the compartment force centers for a second reading of knee joint 10 in the other of flexion and extension. Markers 330A-B and 332A-B correspond to a first movement of the knee joint 10 between flexion and extension. Markers 334A-B correspond to the compartment force centers for another reading of the knee joint 10 in one of flexion and extension and markers 336A-B correspond to the compartment force centers for another reading of knee joint 10 in the other of flexion and extension. Markers 334A-B and 336A-B correspond to a second movement of the knee joint 10 between flexion and extension. In a similar manner, markers 338A-B correspond to the compartment force centers for another reading of the knee joint 10 in one of flexion and extension and markers 340A-B correspond to the compartment force centers for another reading of knee joint 10 in the other of flexion and extension. Markers 338A-B and 340A-B correspond to a third movement of the knee joint 10 between flexion and extension. By maintaining markers for multiple movements of knee joint 10, the operator is able to visualize whether a given change in tibia provisional 228, such as a different shim, or in knee joint 10 is an improvement or not. In one embodiment, the markers for each run are color coded to their respective movement of the knee joint 10. In one embodiment, the markers for each run have different intensities corresponding to their respective movement of the knee joint 10. In one embodiment, older runs are more faded than later runs.

Figure 23:
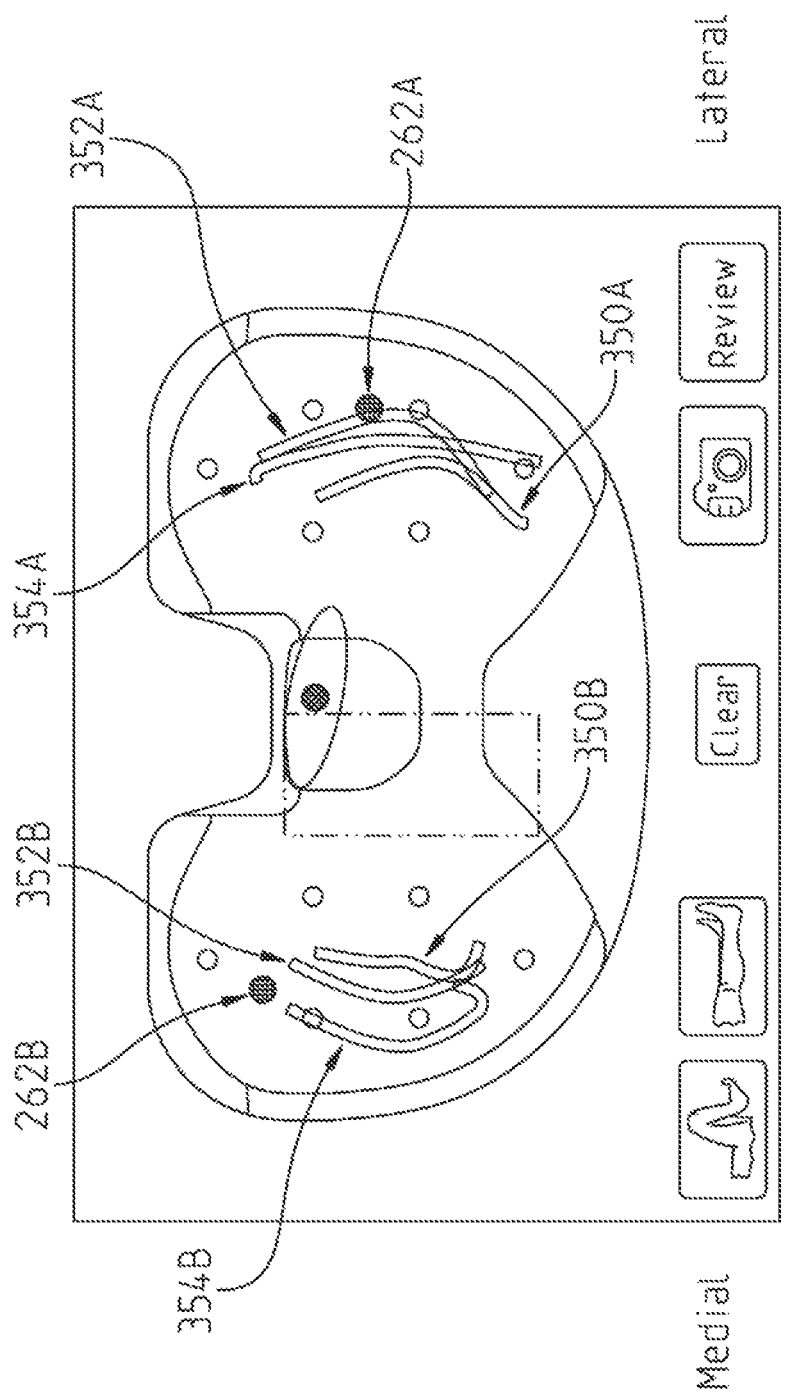
FIG. 23 is a representative view of the exemplary display screen of FIG. 13 wherein the current locations of the force indicators are marked and including historical markers associated with multiple trials of the knee joint at full flexion and full extension and path indicators which provide the relative positions of the force indicators as the knee was at positions between full flexion and full extension for each of the multiple trails.

Referring to FIG. 23, historical paths are maintained by computing system 100 to provide a visual representation to the user of changes in the forces experienced by tibia provisional 228 over time. In the illustrated embodiment, historical paths 350A-B correspond to historical markers 330A-B and 332A-B in FIG. 22. Historical paths 352A-B correspond to historical markers 334A-B and 336A-B in FIG. 22. Historical paths 354A-B correspond to historical markers 338A-B and 340A-B in FIG. 22.

In one embodiment, the operator may capture screenshots by selecting button 246. The screenshots may be replayed by selecting button 248. Each image will be stored chronologically in force data database 116. These images can be replay one at a time by pressing button 248, stored as pre-op or post-op in force data database 116, or scrolled like a slide show. The images can also be downloaded and associated with the patient in patient database 126.

In one embodiment, inputs to the computing system 100 are stored and uploaded to server 156 for later retrieval. Exemplary inputs include recorded force data plus timestamps, any event based info including button presses, screen captures, qualitative surgeon observations, and other suitable information which would permit regeneration of the output of the computing system 100. In one embodiment, the qualitative surgeon feedback may be provided either during the procedure via button presses or vocal indications received through a microphone or after the procedure during a replay of the procedure. Exemplary qualitative surgeon feedback includes qualitative assessments of the fit, such as 'too tight', or 'too loose'. This information may be stored for later retrieval.

Figure 24:
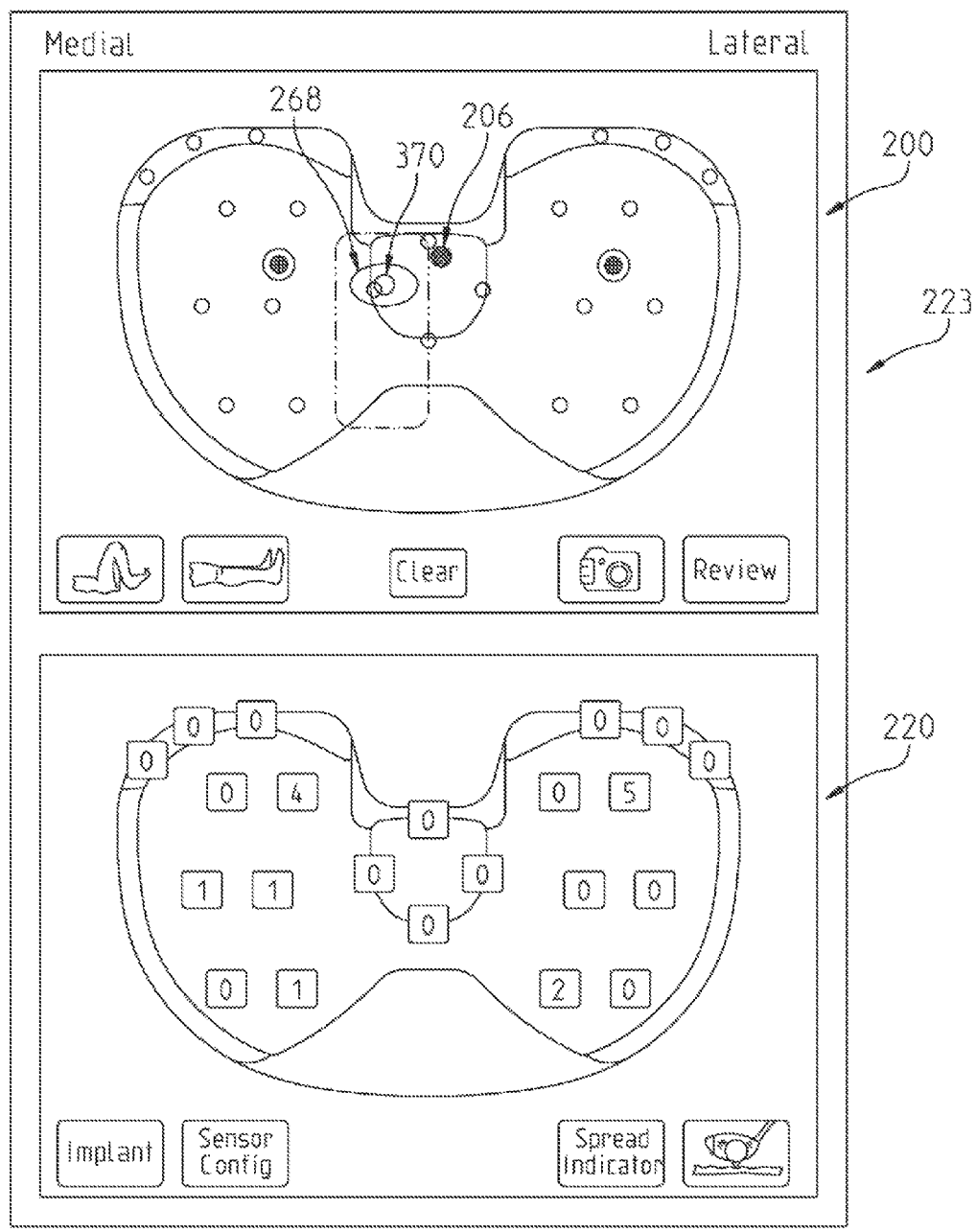
FIG. 24 is an exemplary display screen of a simulation tool.

Turning to FIG. 24, in one embodiment, a display screen 223 is presented including both display screen 200 and display screen 220. In relation to display screen 223, the sensor icons in display screen 220 are inputs whereby an operator may select a given input to increase or decrease a force value. In one embodiment, a right mouse click increases the force and a left mouse click reduces the force. The result of changing the force is shown in the display screen 200 portion of display screen 223. Through display screen 223, computing system 100 is providing a simulation tool for the operator. By manipulating the various force values in display 220, the operator attempts to move mean force center indicator 206 into a given region 370 of bounded area 210. In the illustrated embodiment, mean force center indicator 206 is represented by a golf ball and region 370 is shaped like a hole in a green. As the sensor values are manipulated in display screen 220, the location of mean force center indicator 206 is adjusted.

In one embodiment, as mean force center indicator 206 approaches region 370, sound effects are used to provide feedback. A near miss results in a first sound effect while a successful alignment of mean force center indicator 206 in region 370 results in a second sound effect. By using the simulation tool, as operator becomes more aware of the effect of altering force values in various points of tibia provisional 228. Other exemplary icon changes include a smiley face and frowny face depending on proximity of mean force center indicator 206 to region 370 or thumbs up and thumbs down depending on proximity of mean force center indicator 206 to region 370.

In one embodiment, the simulation tool may provide additional visual indicators. Exemplary visual indicators include a posterior ridge force level indicator, a medial force center indicator, a lateral force center indicator, a post force level indicator, and a spread force indicator.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A computing device, comprising:
a display having a first display screen;
an electronic controller; and
a memory device storing instructions executable by the electronic controller, the instructions being executable by the electronic controller to present a user interface on the first display screen, the user interface comprising:
a two-dimensional representation of an area of a provisional component, positionable between a femur and a tibia and including a plurality of sensors distributed over the area, the plurality of sensors including medical and lateral subsets of sensors, the medial subset of sensors comprising sensors from the plurality that are positioned between a center of the provisional component and a medial side of the provisional component, the lateral subset of sensors comprising sensors from the plurality that are positioned between a center of the provisional component and a lateral side of the provisional component, the representation comprising a medial-lateral direction and an anterior-posterior direction perpendicular to the medial-lateral direction;
a plurality of sensor icons having locations on the first display screen corresponding to the sensor locations on the provisional component; and
a medial force center indicator and a lateral force center indicator having respective positions on the first display screen determined by the electronic controller based on sensed force data and sensor locations from sensors in the medial subset of sensors and the lateral subset of sensors, respectively, the positions variable in the medial-lateral and anterior posterior directions based on force imbalance on the knee joint in the medial-lateral and anterior-posterior directions, respectively.

2. The computing device of claim 1, wherein the user interface further comprises:
an overall force center indicator having a position on the first display screen by the electronic controller based on data from all of the plurality of sensors.

3. The computing device of claim 1, wherein the user interface further comprises:
at least a first bounded region corresponding to a structurally sound knee.

4. The computing device of claim 3, wherein the user interface further comprises:
a first audio indication presented when one of the medial or lateral force center indicators is disposed within the first bounded region.

5. The computing device of claim 3, wherein the user interface further comprises:
a second bounded region disposed within the first bounded region and corresponding to a structurally optimized knee.

6. The computing device of claim 5, wherein the user interface further comprises:
a second audio indication presented when one of the medial or lateral force center indicators is disposed within the second bounded region.

7. The computing device of claim 1, wherein the user interface further comprises:
a representation of a post of the provisional component; and
a plurality of post sensor icons corresponding to sensors from the plurality that are disposed proximate the post.

8. The computing device of claim 7, wherein the plurality of post sensor icons are color-coded to have a first color when the corresponding sensor measures a force value below a threshold value and to have a second color when the corresponding sensor measures a force value above the threshold value.

9. The computing device of claim 1, wherein the user interface further comprises:
a spread indicator comprising a geometric shape displayed around one of the medial or lateral force center indicators, the geometric shape having a size indicative of a magnitude of forces applied to a tibial surface of the provisional component, the geometric shape having a shape indicative of a separation between the medial force center indicator and the lateral force center indicator.

10. The computing device of claim 1, wherein the user interface further comprises:
a path indicator showing a movement of one of the medial or lateral force center indicators as the knee joint moves from a first position to a second position, the path indicator having a first end and a second end corresponding to the first and second positions of the knee joint, respectively.

11. The computing device of claim 10, wherein the path indicator additionally displays clearable historical paths on the first display screen.

12. The computing device of claim 1, wherein the electronic controller communicates wirelessly with the provisional component.

13. The computing device of claim 1, wherein the display further comprises:
a second display screen including the two-dimensional representation of the area of the provisional component, and including icons at respective locations of all of the plurality of sensors, the icons visually indicating forces measured at respective sensors.

14. A computing device, comprising:
a display;
an electronic controller; and
a memory device storing instructions executable by the electronic controller, the instructions being executable by the electronic controller to present a user interface on the display, the user interface comprising:
a two-dimensional representation of an area of a provisional component, positionable between a femur and a tibia and including a plurality of sensors distributed over the area, the plurality of sensors including medial and lateral subsets of sensors, the medial subset of sensors comprising sensors from the plurality that are positioned between a center of the provisional component and a medial side of the provisional component, the lateral subset of sensors comprising sensors from the plurality that are positioned between a center of the provisional component and a lateral side of the provisional component, the representation comprising a medial lateral direction and an anterior-posterior direction perpendicular to the medial-lateral direction; and
a medial force center indicator and a lateral force center indicator having respective positions on the display determined by the electronic controller based on wirelessly received sensed force data and sensor locations from sensors in the medial subset of sensors and the lateral subset of sensors, respectively, the positions variable in the medial-lateral and anterior posterior directions based on force imbalance on the knee joint in the medial-lateral and anterior-posterior directions, respectively.

15. A method for balancing forces in a knee joint, the method comprising:
wirelessly receiving a plurality of sensed values from a corresponding plurality of sensors included in a provisional component, positionable between a femur and a tibia, the plurality of sensors including medial and lateral subsets of sensors, the medial subset of sensors comprising sensors from the plurality that are positioned between a center of the provisional component and a medial side of the provisional component, the lateral subset of sensors comprising sensors from the plurality that are positioned between a center of the provisional component and a lateral side of the provisional component, the sensors having respective locations on an area of the provisional component, the area of the provisional component having a medial-lateral direction and an anterior-posterior direction perpendicular to the medial-lateral direction, each sensed value being indicative of a force applied against the provisional component at the respective sensor location;
displaying on a display a two-dimensional representation of the area of the provisional component;
displaying on the display a plurality of sensor icons having locations on the display corresponding to the sensor locations on the provisional component;
displaying on the display a plurality of sensor icons having locations on the display corresponding to the sensor locations on the provisional component;
displaying on the display a medial force center indicator and a lateral force center indicator, the medial and lateral force center indicators having respective positions on the display determined from the received sensed values from the medial subset of sensors and the lateral subset of sensors, respectively, weighted by the locations of the respective sensors, the positions variable in the medial-lateral and anterior-posterior directions based on force imbalance on the knee joint in the medial-lateral and anterior-posterior directions, respectively;
displaying on the display a bounded region corresponding to a structurally sound knee; and
providing the display as visual feedback for a practitioner during knee surgery in which the forces become balanced in the knee joint, the balancing occurring when the force center indicator becomes positioned within the bounded region.

16. The computing device of claim 14, wherein the user interface further comprises:
a plurality of sensor icons having locations on the display corresponding to the sensor locations on the provisional component.

* * * * *

UNITED STATES PATENT AND TRADEMARK OFFICE
CERTIFICATE OF CORRECTION

PATENT NO. : 9,539,116 B2  
APPLICATION NO. : 13/819116  
DATED : January 10, 2017  
INVENTOR(S) : Claypool et al.

Page 1 of 1

It is certified that error appears in the above-identified patent and that said Letters Patent is hereby corrected as shown below:

On page 2, in Column 2, under "Foreign Patent Documents", Line 20, delete "20120240406" and insert --2010240406-- therefor Signed and Sealed this  
Third Day of April, 2018

Andrei Iancu  
*Director of the United States Patent and Trademark Office*